US006306583B1

(12) United States Patent
Livi et al.

(10) Patent No.: US 6,306,583 B1
(45) Date of Patent: Oct. 23, 2001

(54) HUMAN BRAIN PHOSPHODIESTERASE

(75) Inventors: George P. Livi, Havertown; Megan M. McLaughlin, Drexel Hill; Theodore J. Torphy, Bryn Mawr, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 08/445,474

(22) Filed: May 22, 1995

Related U.S. Application Data

(63) Continuation of application No. PCT/US94/02612, filed on Mar. 10, 1994, which is a continuation of application No. 08/029,334, filed on Mar. 10, 1993, now abandoned.

(51) Int. Cl.[7] .............................. C12Q 1/68; C12Q 1/44; C12N 9/16

(52) U.S. Cl. .................. 435/6; 435/19; 435/196

(58) Field of Search ........................ 435/196, 6, 172.3, 435/19

(56) References Cited

U.S. PATENT DOCUMENTS 5,527,826 * 6/1996 Wigler et al. ........................ 536/23.5

FOREIGN PATENT DOCUMENTS

91/16457 * 10/1991 (WO) .

OTHER PUBLICATIONS

McHale et al. Expression of human recombinant cAMP phosphodiesterase isozyme IV reverses growth arrest phenotypes in phosphodiesterase deficient yeast. Mol. Pharamacol. 39(2):109–113, Feb. 1991.*

Schmiechen et al. Close correlation between behavioural response and binding in vivo for inhibitors of the rolipram sensitive phosphodiesterase. Psychopharmacology 102(1):17–20, 1990.*

Shelton et al, H 442 "1992 Keystone Symposia", *Journal of Cellular Biochemistry*, Supplement 16B, 1992.

* cited by examiner

*Primary Examiner*—Christopher S. F. Low
*Assistant Examiner*—Gabriele E. Bugaisky
(74) *Attorney, Agent, or Firm*—Elizabeth J. Hecht; Edward R. Gimmi; Charles M. Kinzig

(57) ABSTRACT

Isolated cDNA clones from human brain (frontal cortex) cDNA libraries that encode a unique subtype of the low $K_m$, cAMP-specific phosphodiesterases (PDE IVs) are disclosed. Analysis of the distribution of hPDE $IV_B$ mRNA expression in various human tissues using a nonconserved fragment of the cDNA as a probe revealed a restricted pattern of expression, with an ~4-kb mRNA detected in brain, heart, lung and skeletal muscle and not in placenta, liver, kidney or pancreas. Furthermore, an additional ~5-kb hPDE $IV_B$-related mRNA species was detected in brain tissue. Expression of hPDE $IV_B$ in a genetically-engineered PDE-deficient strain of the yeast *Saccharomym cerevisiae* resulted in the overproduction of cAMP PDE activity which displayed the expected kinetic characteristics for a PDE IV: 1) low $K_m$ (4.3 $\mu$M) for cAMP, 2) high $K_m$ (>3 mM) for cGMP, and 3) sensitivity to rolipram ($K_i$=0.085 $\mu$M), a selective inhibitor of PDE IV. Recombinant hPDE $IV_B$ also bound [$^3$H] R-rolipram saturably and with a high affinity. Analysis of [$^3$H] R-rolipram binding data revealed curvilinear Scatchard plots, suggesting the presence of two non-interacting high affinity rolipram binding sites ($K_d$=0.4 and 6 nM) or a negatively cooperative interaction among multiple binding sites.

This novel enzyme is particularly useful for screening candidate compounds for their ability to serve as potential anti-depressant, antiasthmatic or anti-inflammatory agents.

10 Claims, 9 Drawing Sheets

FIG. 1A

```
TCT GTG TTG GAA AAT CAT CAC CTT GCT GTG GGT TTC AAA CTG CAA GAA CAC TGT GAC ATC TTC ATG AAT    975
Leu Thr Lys Glu Asn His His Leu Ala Val Gly Phe Lys Leu Gln Glu His Cys Asp Ile Phe Met Asn    350
CTC ACC AAG AAG CAG CGT CAG ACA CTC CAG AGG AAG CTC ATT GAC GTT TTA GCA ACT GAT ATG TCT AAA CAT   1050
Leu Thr Lys Lys Gln Arg Gln Thr Leu Gln Arg Lys Leu Ile Asp Val Leu Ala Thr Asp Met Ser Lys His   375
ATG AGC CTG GCA GAC CTG AAG CTG GAA ACG ATG GTA GAA AAA GTT ACA AGT TCA GGC GTT CTT CTC CTA GAC   1125
Met Ser Leu Ala Asp Leu Lys Leu Glu Thr Met Val Glu Lys Val Thr Ser Gly Val Leu Leu Leu Asp    400
AGC TAT ACC GAT CGC ATT CAG GTC CTT GTA GAA AAC ATG GTA CAC TGT GCA GAC CTG AGC AAC CCC AAG TCC TTG   1200
Asn Tyr Thr Asp Arg Ile Gln Val Leu Val Glu Asn Met Val His Cys Ala Asp Leu Ser Asn Pro Thr Lys Ser Leu   400
AAC TAT ACC GAT CGC ATT CAG GTC CTT GTA GAA AAC ATG GTA CAC TGT GCA GAC CTG AGC AAC CCC AAG TCC TTG   1200
Asn Tyr Thr Asp Arg Ile Gln Val Leu Val Glu Asn Met Val His Cys Ala Asp Leu Ser Asn Pro Thr Lys Ser Leu   400
GAA TTG TAT CGG CAA TGG ACA GAC CGC ATC ATG GAG GAA TTT TTC CAG CAG GGA GAC AAA GAG CGG GAG AGG GGA   1275
Glu Leu Tyr Arg Gln Trp Thr Asp Arg Ile Met Glu Glu Phe Phe Gln Gln Gly Asp Lys Glu Arg Glu Arg Gly   425
ATG GAA ATT AGC CCA ATG TGT GAT AAA CAC ACA GCT TCT GTG GAA GTT GGT TTC ATC GAC TAC ATT   1350
Met Glu Ile Ser Pro Met Cys Asp Lys His Thr Ala Ser Val Glu Val Gly Phe Ile Asp Tyr Ile    450
GTC CAT CCA TTG GAG TGG GAG ACA TTG CAG ACA CTT GAG GCA GAT TTG CAG CCT CAG GTT CTG GAT ACC TTA GAA GAT   1425
Val His Pro Leu Glu Trp Glu Thr Leu Gln Thr Leu Glu Ala Asp Leu Gln Pro Gln Val Leu Asp Thr Leu Glu Asp   475
AAC AGG AAC TGG TAT CAG AGC ATA CCT CAA AGT CCC TCA CCA CTG GAC AAC AGG GAC TGC CAG   1500
Asn Arg Asn Trp Tyr Gln Ser Ile Pro Gln Ser Pro Ser Pro Leu Asp Asn Arg Asp Cys Gln    500
GGT CTG ATG GAG AAG TTT CAG TTT GAA CTG ACT CTC TGT GTT CTT GAT GAG GAA GAT TCT GAA GGA GAA CCT GAG GGA GAG   1575
Gly Leu Met Glu Lys Phe Gln Phe Glu Leu Thr Leu Cys Val Leu Asp Glu Glu Asp Ser Glu Gly Glu Pro Glu   525
GGA CAC AGC TAT TTC AGC ACA AAG ACA ACG CTT TGT GTG ATT GAT CCA GAA AAC AGA GAT TCC CTG GGA GAG ACT   1650
Gly His Ser Tyr Phe Ser Thr Lys Thr Thr Leu Cys Val Ile Asp Pro Glu Asn Arg Asp Ser Leu Gly Glu Thr   550
Asp Ile Asp Ile Ala Thr Glu Asp Lys Asp Lys Ser Pro Val Asp Thr ***     564
GAC ATA GAC ATT GCA ACA GAA GAC AAG GAC AAG TCC CCC GTG GAT ACA TAA TCCCCCTCCTCCCTGTGGAGATGAACATTCTATCCTTGAT   1734
GAGCATGCCAGCTAGTGGTAGGCCAGCCATGGGGCCAAGACCTGCACAGGACAGCAAGGGCCACCTGGCTTTCAGTTACTTGAGTTTGGAGTCAG   1833
AAAGCAAGACCAGAAGCAGCTAGCAGCAAATAGCAGCTTGAGCTTGATGGCCTTGATGCTTGCAAGCTTGTGCAAGCTTGTGCTGTTGCTGGGGC   1932
CGATTCTGACTAATAACTTCATTATGAATCTTCTCACTTGTCCCTTTGTCTGCCAACTTGTGTGACAACTTTTTTGACTCTTTGACAAACATTTCAAGTGGAACTTATCCCGACAGTGACTGAAC   2031
TCACTGACTAATAACTTCATTATGAATCTTCTCACTTGTCCCTTTGTCTGCCAACTTGTGTGACAACTTTCAAGTTGACAACTTTTTTTGTAAAACATTTCATGTCTTTAAAATGC   2130
CTGTTGAATAACCTGGAGTTTAGTAGTAATATCCTTACTTACTTACTTACTTTGCAAACAGACAGAAGGATACACTTCTAACACACTTTACTTCCTTCCCCT   2229
CTTCCTTCTTTCTTGGGCAATATCCCACAGTCACTCTTAAAACTtctctctctgtttgcctgcccaacagtacttttaactttttgctgtaaacagaataaatagt   2328
GTTGTCCAGTCCAACTCCAGTCCACAGTCACTCTTAAAACTtctctctctgtttgcctgcccaacagtacttttaactttttgctgtaaacagaataaattga   2427
```

FIG. 1B

```
acaaattaggggtagaaggagcagtggtgtcgttcaccgtgagagtctgcatagaactcagcagtgccctgctgtcttggacctgcccca        2526
caggagttgtacagtccctgccctgctccctactcctctcttcaccccgttaggctgttttcaatgtaatgctgccgtcctcctcttgcactgcctt        2625
ctgcgctaacacctccattcctgtttattacctgtatttattatttaattatgtttgtaagttttgtattgttgtattatatctaacattg        2724
cctgccaatggtggtgttaaatttgtgtagaaaactctgcctaagagttacgactttttcttgtaatgttttgtattgtgtattataaccaaacgt    2823
cacttagtagagacatatggccccctggccccttggcagggacaggggtgggctttgttcaaagggtctgcctttcctgctgagttgctacttctgcac  2922
aaccctttatgaaccagttttgggaaacaatagtccacacattagatactaaatggtttatactgagcttttactttgtatagcttgatagggcagg    3021
gggcaatggatggtagtttttacccagttctatccaaatctatgtgggcatgagtctcccgaactactgacttgaagaggtagcctctttgcttggtg  3120
aggaaacactacatttgctcacagatgattcttctgaatgtcccgaactactgacttgaagaggtagcgccattaagcaggaatgtca           3219
tgttccagttcattacaaagaacaatgtgaatttttataataaacaatgtgaactgatgtagcaaatgaactttcatgcttcagcatgtgactcagta  3318
gataacacttgttaggcctcttactgatgtctatgtcagtctcagtttcaaatatgttcatgctttcagcattgtgactgtgactaatacagaaatg   3417
gcacaaatgtgcatgaccaatgtatgtctatgaacactgcattgtttcaggtggacatttatcgattttcaaatgttctcacaatgtatgttatagt   3516
gttattattatatattgtgttcaatgcattctaaagagactttatatgaggtgaataaagaaaagcataattaaaaaaaaaaaaaaaaa             3609
```

FIG. 1C

```
          1
hPDE IVB  ..MKEHGGTF SSTGISGGSG DSAMDSLQPL QPNYMPVCLF AEESYQKLAM ETLEELDWCL    58
hPDE IVA  .......... .......MC PFPVTTVPLG G-TPVCKATL S--TC-Q--R ----------
rPDE IVA  .......... .......... .......... .......... .........M ----------
rPDE IVB  ....SLRIVR NNFTLLTNLH GAPNKRSPAA SQAPVTRVS- Q--------- ----------

59
hPDE IVB  DQLETIQTYR SVSEMASNKF ..KRMLNREL THLSEMSRSG NQVSEYISNT FLDKQNDVEI   116
hPDE IVA  E----M---- -------H-- .......... .......... ----T----- ----------
rPDE IVA  PLVDFFCETC -KPWLVGWWD QF---I---- .......... ----E----- ----------
rPDE IVB  ---------- ---------- .......... .......... ---------- ----------

117
hPDE IVB  PSPTQKDREK KKKQQ..... ..APR PRPSQPPPPP VPHLQP-SE- LMTQI SGVKKLMHSS SLNNTSIFRF   156
hPDE IVA  -----M-E-- .......... ...... .......... .......... T-L------- ----N---- ----SN-P--
rPDE IVA  ----PRQ-AF .......... ...... .....PPPSV LRQSQP-S-- T-L---V-TG ---------- ----NVP---
rPDE IVB  ---------- .......... ...... .......... .......... ---------- ---------- ----------

157
hPDE IVB  GVNTENEDHL AKELEDLNKW GLNIFNVAGY SHNRPLTCIM YAIFQERDLL KTFRISSDTF   216
hPDE IVA  --K-DQ-EL- -Q---N---- -----C-SD- AGG-S----- ---M------ ---K---PV--M
rPDE IVA  ---------- -Q---N-S-- -----C-SE- AGG-S-S--- ---T------ ---K-H-PV--M
rPDE IVB  ---------- ---------- ---------- ---------- ---------- ---K------
```

FIG. 2A

```
         217
hPDE IVB ITYMMTLEDH YGSDVAYHNS LHAADVAQST HVLLSTPALD AVFTDLEILA AIFAAAIHDV   276
hPDE IVA V---L----- --A------- ------L--- ---A------ ---------- -L--------
rPDE IVA MM--L----- --A------- ------L--- ---A------ ---------- -L--------
rPDE IVB V--------- ---------- ---------- ---------- ---------- ----------

277
hPDE IVB DHPGVSNQFL INTNSELALM YNDESVLENH HLAVGFKLLQ EEHCDIFMNL TKKQRQTLRK   336
hPDE IVA ---------- ---------- ---------- -------YN- -----Q---- --S-R-----
rPDE IVA ---------- ---------- ---------- --------N- -----Q---- --S-R-----
rPDE IVB ---------- ---------- ---------- ---------- -----Q---- ----------

337
hPDE IVB MVIDMVLATD MSKHMSLLAD LKTMVETKKV TSSGVLLLDN YTDRIQVLRN MVHCADLSNP   396
hPDE IVA ---------- ----T----- ---------- ---------- -S-------- ----------
rPDE IVA ---------- ----T----- ---------- ---------- -S-------- ----------
rPDE IVB ---------- ---------- ---------- ---------- ---------- ----------

397
hPDE IVB TKSLELYRQW TDRIMEEFFQ QGDKERERGM EISPMCDKHT ASVEKSQVGF IDYIVHPLWE   456
hPDE IVA ---P------ -----A---- ---R------ ---------- ---------- ----------
rPDE IVA ---P------ -----A---- ---R------ ---------- ---------- ----------
rPDE IVB ---------- ---------- ---------- ---------- ---------- ----------
```

```
         457
hPDE IVB TWADLVQPDA QDILDTLEDN RNWYQSMIPQ SPSPPLDEQN RDC..QGLME KFQFELTLDE  514
hPDE IVA -------H--- ---------- -D--Y-A-R- -----PE-ES -GPGHPP-PD --------E-
rPDE IVA -------H--- ---------- -D--H-A-R- -----E-EP  GGLGHPS-PD --------E-
rPDE IVB ---------- ---------- ---------- ---------RS .......... --------E-

515                                                           564
hPDE IVB EDSEGPEKEG EGHSYFSSTK TLCVIDPENR DSLGETDIDI ATEDKSPVDT ..........
hPDE IVA -E....-E-. ISRAQIRC-A QEALTEQGLS GVEEAL-AT- -W-ASPAQES LEVHAQEASL
rPDE IVA -E.....EDS LEVPGLPT.. ....TEETFL AAEDARAQAV DWSKFKGPS- TVVEVAERLK
rPDE IVB ---------- --PD------ ---------- ---E------ ------LI-- ..........

hPDE IVB .......... .......... .......... .......... .......... ..........
hPDE IVA EAELEAVYLT QQAQSTGSEP VAPDEFSNRE EFVVAVSHSS PSALALQSPL LPAWRTLSVS
rPDE IVA QETASAYGAP QESMEAVGCS FSPGTPILPD VRTLSSSEEA PGLLGLPSTA AEVEAPRDHL
rPDE IVB .......... .......... .......... .......... .......... ..........

hPDE IVB .......... .......... .......... .......... ..........
hPDE IVA EHAPGLPGLP STAAEVEAQR EHQAAKRACS ACAGTFGEDT SALPAPGGGG SGGDPT
rPDE IVA AATRACSACS GTSGDNSAII STPGRWGSGG DPA....... ..........
rPDE IVB .......... .......... .......... .......... ..........
```

HUMAN BRAIN PHOSPHODIESTERASE

This is a continuation of PCT application Ser. No. PCT/US94/02612 filed Mar. 10, 1994 which is a continuation U.S. Ser. No. 08/029,334 filed on Mar. 10, 1993, now abandoned.

FIELD OF THE INVENTION

This invention relates to cDNAs encoding phosphodiesterases (PDEs), their use in the recombinant production of the enzyme and the use of the PDE in drug screening. More specifically this invention relates to a unique subtype of a human, low $K_m$, cAMP-specific phosphodiesterase (PDE IV) and its use in the screening of pharmaceutically useful substances.

BACKGROUND OF THE INVENTION

The recent identification and characterization of cDNA clones encoding several different mammalian PDEs has supported the cumulative biochemical evidence for the existence of multiple isozyme families as well as the number and tissue distribution of particular subtypes (Livi, G. P. et al., *Mol. Cell. Bio.* 10:2678–86 (1990); Colicelli, J. et al., *Proc. Natl. Acad. Sci*: (*USA*) 86:3599–3603 (1989) and Davis et al., *Proc. Natl. Acad. Sci.*, (*USA*) 86:3604–08 (1989)). A particularly interesting isozyme family with respect to drug discovery is the PDE IV family. There is considerable evidence to suggest that this isozyme family represents a molecular target for a variety of therapeutic agents ranging from anti-depressants (Nicholson, C. D. et al., *Trends in Pharm. Sci.*, 12:14–27 (1991)) to anti-asthmatic and anti-inflammatory agents (Torphy, T. J. and B. J. Undem, *Thorax* 46:512–23 (1991)). The cloning, expression and biochemical characteristics of hPDE $IV_A$, an enzyme encoded by a cDNA obtained from a human monocyte library has been reported (Livi, G. P. et al. supr (1990) and Torphy T. J. et al., *J. Biol. Chem.* 267:1798–1804 (1992)). The purpose of this invention is to provide cloned and characterized PDE IV subtypes expressed in human brain.

Cyclic nucleotide phosphodiesterases (PDEs) consist of a family of enzymes that catalyze the hydrolysis of 3',5'-cyclic nucleotides, resulting in the formation of 5'-nucleotide metabolites. At least five distinct mammalian PDE isozyme families exist, each distinguished on the basis of a number of biochemical properties including 1) enzyme kinetics, 2) substrate selectivity, and 3) selective inhibition by various compounds. These isozyme families are defined as: 1) the $Ca^{2+}$/calmodulin-dependent PDEs; II) the cGMP-stimulated PDEs; III) the cGMP-inhibited PDEs; IV) the cAMP-specific PDEs and V) the cGMP-specific PDEs (Beavo, J. A. et al., *Trends Pharmacol. Sci.* 11:150–155(1990) and Conti, M. et al., *Endocrine Rev.* 12:218–234 (1991)).

There is considerable interest in evaluating inhibitors of the low-$K_m$, cAMP-specific PDEs (PDE IVs) as potential anti-inflammatory and anti-asthmatic drugs. As mentioned above, the cloning and expression of a cDNA that encodes a human PDE IV subtype expressed in monocytes (hPDE $IV_A$) has been reported. This enzyme exhibited significant amino acid sequence homology to PDE IVs from rat brain (Colicelli, supra (1989)) and *Drosophila* (Chen, C-N. et al., *Proc. Nat'l. Acad. Sci. USA* 83:9313–17 (1986)). Furthermore, the recombinant enzyme was overexpressed in both yeast and mammalian cells and defined as a PDE IV based on its kinetic characteristics and sensitivity to isozyme-selective inhibitors. Recombinant hPDE $IV_A$ possesses a low $K_m$ for cAMP ($K_m$=3.2 μM), a high $K_m$ for cGMP, and is inhibited by rolipram ($K_i$=0.06 μM) but not by selective inhibitors of other PDE isozymes.

It has been proposed that the anti-depressant activity of the PDE IV-selective inhibitor rolipram is associated with the inhibition of PDE IVs in the central nervous system. Rolipram binds with high affinity to rat brain homogenates and it has been assumed that this binding site represents either a catalytic or allosteric site within the PDE IV molecule itself Accordingly, it has been recently established that recombinant hPDE $IV_A$ possesses both catalytic activity and a high affinity ($K_d$=2 nM) [$^3$H]-rolipram binding site (Torphy T. J. et al., *J. Biol. Chem.* 267:1798–1804 (1992)). Although the relationship between this high affinity binding site and the catalytic activity of hPDE $IV_A$ is not clear, it has been proposed that this site may represent either an allosteric site or the catalytic site on one of two distinct catalytic forms of the enzyme. It is of considerable interest to know if an additional PDE IV subtype is expressed in human brain, and if so, whether this subtype has biochemical characteristics similar to hPDE $IV_A$. Of particular interest is the determination whether the high affinity rolipram binding site exists on PDE IV subtypes in addition to hPDE $IV_A$.

Although the mechanism of action of rolipram can be assessed biochemically using the available recombinant PDE IV enzymes derived from human monocytes and rat brain, a true pharmacological understanding of how PDE IV activity (as well as cellular cAMP content) regulates neurobiochemical processes is limited by lack of knowledge regarding PDE IV subtypes expressed in the human brain, if any. Accordingly, it is a purpose of this invention to provide isolated cDNA clones encoding PDE IV from human brain and to employ this valuable reagent in a screening protocol for the discovery of subtype-specific PDE IV inhibitors. Disclosed herein is the cloning of a cDNA from a human frontal cortex cDNA library that encodes a unique PDE IV subtype. This enzyme is designated as hPDE $IV_B$ according to the nomenclature of Beavo and Reifsnyder supra (1990). The cDNA product is defined as a type IV PDE based on its comparative amino acid sequence as well as PDE IV-selective inhibitors, the kinetic characteristics and the [$^3$H] rolipram binding capacity of the recombinant enzyme. Surprisingly, this PDE $IV_B$ subtype exhibits a restricted tissue-type pattern of expression.

BRIEF DESCRIPTION OF THE INVENTION

This invention provides an isolated nucleic acid molecule encoding a human PDE $IV_B$. This invention also provides a human PDE $IV_B$ substantially free of other proteins of human origin. The invention also provides molecular reagents such as cloning and expression vectors for the recominbinant production of the PDE $IV_B$ enzyme. The invention also provides recombinant host cells capable of expressing the enzyme. The invention further includes a method for identifying ligands capable of binding to a PDE $IV_B$ enzyme comprising: contacting a PDE $IV_B$ enzyme with a plurality of candidate ligands labeled with an analytically detectable reagent under conditions sufficient for ligand binding and identifying those ligand candidates capable of enzyme binding by detecting the presence of a labeled ligand/enzyme complex. The invention also provides a method of screening compounds to identify those compounds which bind to a human PDE $IV_B$ enzyme comprising contacting the enzyme with (a) a plurality of drug candidates in the presence of (b) an analytically detectable ligand known to bind to the enzyme, under conditions that permit binding of (a) and (b) to the enzyme, and identifying those candidate compounds capable of enhancing or inhibiting the binding or interaction of the known ligand with the enzyme. The invention also provides for detecting candidate compounds capable of inhibiting the catalytic activity of the enzyme by monitoring the effect of the compound on the ability of the enzyme to hydrolyze substrates (e.g., cAMP). The invention also provides biological screening assay for the detection of PDE IV$_B$ selective ligands comprising: (a) providing a PDE deficient host cell that exhibits a specific growth arrest phenotype associated with elevated cAMP levels; (b) transforming or transfecting said host cell with the plasmid capable of directing the expression of a PDE IV$_B$ enzyme and culturing the resultant recombinant host cell under conditions sufficient for the expression of PDE IV$_B$ enzyme and sufficient to generate a growth arrest response should the expressed PDE IV$_B$ enzyme be inhibited; (c) contacting the recombinant host cell with a plurality of candidate compounds and (d) identifying those compounds which are capable of inhibiting the enzyme and thereby unmasking the growth arrest phenotype. The invention also contemplates pharmacuetical compositions comprising a compound identified by any of the three above-mentioned methods and a pharmaceutically acceptable carrier. The invention further includes antisense oligonucleotides having sequence capable of binding specifically with any sequence of an mRNA molecule which encodes the human PDE IV$_B$ so as to prevent the translation thereof. The invention also provides antibodies directed to the human PDE IV$_B$. The invention also provides a fusion protein comprising a PDE IV$_B$ domain and an cell surface localizing domain and a method of screening compounds to identify those compounds which bind to a human PDE IV$_B$ enzyme comprising contacting recombinant host cells expressing on the surface thereof the fusion protein with a plurality of drug candidates, under conditions to permit binding to the PDE IV$_B$ domain, and identifying those candidate drugs capable of enhancing or inhibiting the catalytic activity of the enzyme.

BRIEF DESCRIPTION OF THE FIGURES

Figure 1A:
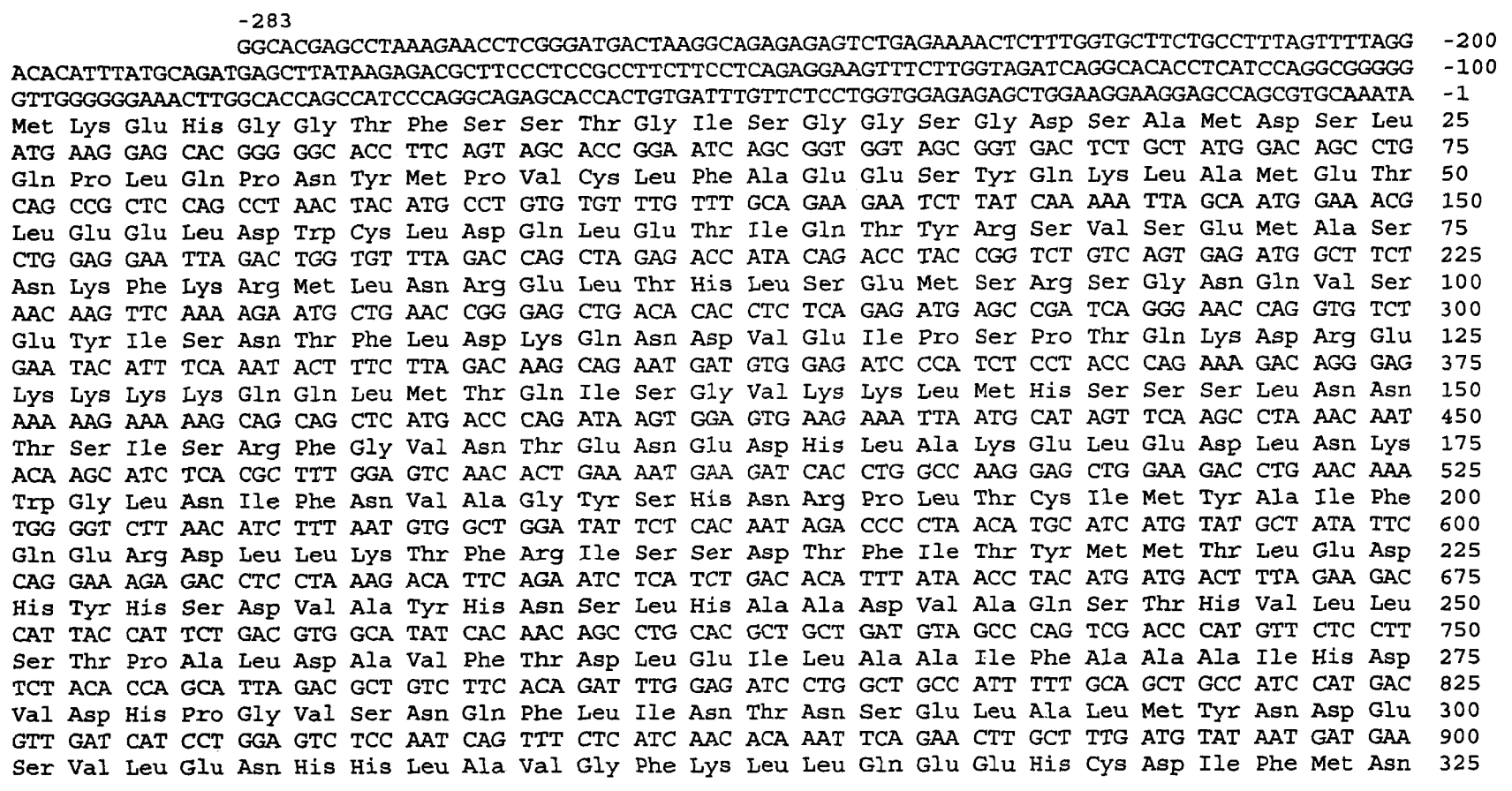

FIGS. 1A, 1B, and 1C illustrate the composite nucleotide sequence of the hb-PDE1a and hb-PDE1 cDNA clones with the predicted hPDE IV$_B$ amino acid sequence. The entire coding sequence, as well as the complete 5' and 3'-UTRs, are shown. Coordinates at the right indicate nucleotide and amino acid positions. The amino acid sequence is shown starting from the putative translation initiation site (+1), and asterisks show the putative termination codon. Upper case letters correspond to clone hb-PDE1, whereas lower case letters correspond to nucleotides unique to clone hb-PDE1a (see Examples). The underlined region represents a non-conserved region (see FIGS. 1A, 1B, and 1C illustrate) that was used as a probe for the Northern analysis shown in FIG. 5A. The hb-PDE1 cDNA extends from positions −283 to 2363, whereas hb-PDE1a extends from positions 1008 to 3609. The putative polyadenylation signal (5'-AATAAA-3') and poly (A) tract are bolded. The GenBank accession No. is M97515.

FIGS. 2A, 2B, and 2C illustrate the deduced amino acid sequence alignment of representative mammalian low-K$_m$ cAMP-specific PDEs (PDE IVs). hPDE IV$_B$ is the human brain PDE IV subtype reported here; hPDE IV$_A$ is a human monocyte PDE IV; rPDE IV$_A$ and rPDE IV$_B$ represent two distinct rat brain PDE IVs derived from the cDNA clones RD1 and DPD, respectively. Dashes indicate identical amino acids sequences; periods indicate sequence gaps included to maximize alignments.

FIG. 3A, double-reciprocal plot of cAMP hydrolysis. The concentrations of cAMP used ranged from 0.03 to 50 μM. The K$_m$ for cAMP was calculated to be 4.3±0.2 μM and the V$_{max}$ was 11.3 nmol/mg protein/min. Data obtained with the 10 highest concentrations of cAMP are shown on an expanded scale in the inset.

DETAILED DESCRIPTION OF THE INVENTION

Figures 1, 3A:
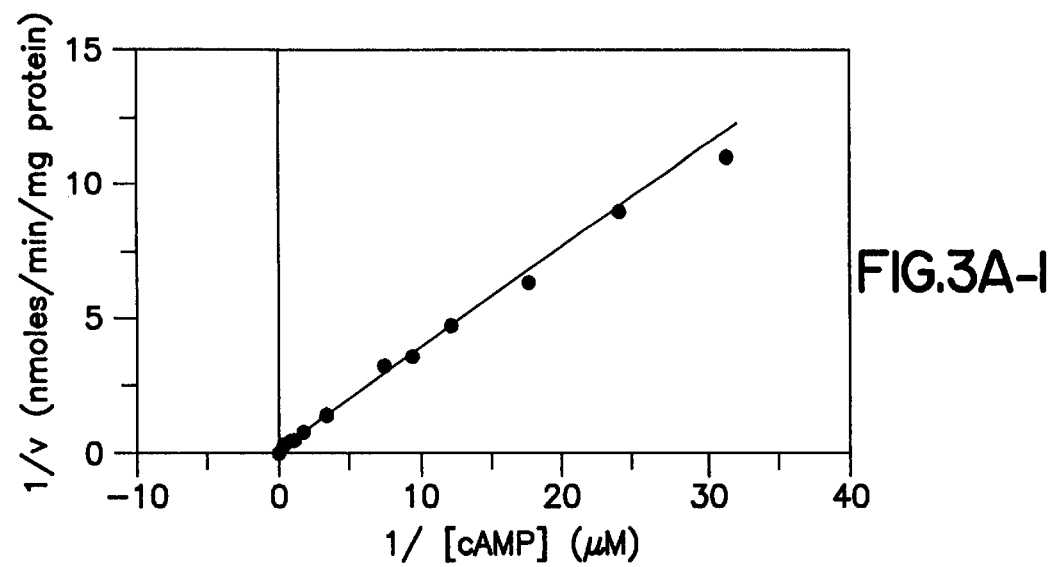
FIG. 3A–1 and 3A–2 illustrate the kinetics of hPDE IV$_B$ cAMP hydrolysis and inhibition by rolipram. PDE activity was assessed in yeast lysates 6 hr after hPDE IV$_B$ expression was induced. The data are representative of results from two separate preparations.

In describing the present invention, the following terms will be employed, and are intended to be defined as indicated below.

An "antigen" refers to a molecule containing one or more epitopes that will stimulate a host's immune system to make a humoral and/or cellular antigen-specific response. The term is also used herein interchangeably with "immunogen."

The term "epitope" refers to the site on an antigen or hapten to which a specific antibody molecule binds. The term is also used herein interchangeably with "antigenic determinant" or "antigenic determinant site."

"Fusion protein" is a protein resulting from the expression of at least two operatively-linked heterologous coding sequences. The protein comprising a PDE IV$_B$ peptide and a second unrelated peptide sequence is an example of a fusion protein.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a coding sequence. For purposes of defining the present invention, the promoter sequence is bounded at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalendy linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" or "substantially the same" when at least about 93% (preferably at least about 95%, and most preferably at least about 98%) of the nucleotides or amino acids match over a defined length of the molecule, normally the entire length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., "Current Protocols in Mol. Biol." Vol. I & II, Wiley Interscience. Ausbel et al. (ed.) (1992). Protein sequences that are substantially the same can be identified by proteolytic digestion, gel electrophoresis and microsequencing.

The term "functionally equivalent" intends that the amino acid sequence of the subject protein is one that will elicit a catalytic response substantially equivalent to the specified PDE $IV_B$ peptide.

A "heterologous" region of a DNA construct is an identifiable segment of DNA within or attached to another DNA molecule that is not found in association with the other molecule in nature. Thus, when the heterologous region encodes a receptor gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A "high affinity" rolipram binding site is characterized by a $K_i$ for rolipram of about 10 nM or less, whereas a "low affinity" rolipram binding site is characterized by a $K_i$ for rolipram of about 100 nM or greater.

The term ligand as used herein means any molecule that can bind or interact with the PDE $IV_B$ enzyme. When a ligand binds to the active site of the enzyme and is catalytically acted upon, the ligand is known as a substrate. Inhibitors are ligands which may or may not bind at the active site of the enzyme.

This invention provides an isolated nucleic acid molecule encoding a human PDE $IV_B$. Such an enzyme is defined by the criteria discussed above for members of this unique subtype. One means for isolating a human PDE $IV_B$ coding nucleic acid is to probe a human genomic or cDNA library with a natural or artificially designed probe using art recognized procedures (See for example: "Current Protocols in Molecular Biology", Ausubel, F. M., et al. (eds.) Greene Publishing Assoc. and John Wiley Interscience, New York, 1989,1992). One particularly useful probe for this purpose is a probe incorporating all, or a hybridizable fragment, of a DNA of the sequence disclosed herein as Seq. ID. No. 1. Alternatively, as describe hereinbelow, probes from PDE $IV_A$ may also be used. The isolated nucleic acid molecules obtained hereby may be used to obtain complementary copies of genomic DNA, cDNA or RNA from human, mammalian or other animal sources or to screen such sources for related sequences including transcriptional regulatory and control elements defined above as well as other stability, processing, translation and tissue specificity-determining regions from 5' and/or 3' regions relative to the coding sequences disclosed herein. Additional coding sequences isolated by the procedures disclosed herein are considered to be substantially the same as the coding sequence given in Seq. ID. No. 1 if the additional sequence shares about 93% homology with the sequence of Seq. ID. No. 1.

This invention also provides for an isolated protein which is the human PDE $IV_B$. This enzyme is defined with reference to the amino acid sequence listed in Seq. ID. No. 2 and includes variants with a substantially homologous amino acid sequence but retaining the criteria of a PDE $IV_B$ enzyme identified herein. The proteins of this invention are preferably made by recombinant genetic engineering techniques. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g., yeast or mammalian) cells by methods well known in the art (Ausubel et al., supra). The coding sequences for the desired proteins having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage $\lambda$(E. coli), pBR322 (E. coli), pACYC177 (E. coli), pKT230 (gram-negative bacteria), pGV1106 (gram-negative bacteria), pLAFR1 (gram-negative bacteria), pME290 (non-E. coli gram-negative bacteria), pHV$^{14}$ (E. coli and Bacillus subtilis), pBD9 (Bacillus), pIJ61 (Streptomyces), pUC6 (Streptomyces), YIp5 (Saccharomyces), a baculovirus insect cell system, YCp19 (Saccharomyces). See, generally, "DNA Cloning": Vols. I & II, Glover et al. ed. IRL Press Oxford (1985) (1987) and; T. Maniatis et al. "Molecular Cloning" Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the E. coli tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include thqse which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular antigen of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. It may also be desirable to produce mutants or analogs of the receptors of interest Mutants or analogs may be prepared by the deletion of a portion of the sequence encoding the protein, by insertion of a sequence, and/or by substitution of one or more nucleotides within the sequence. Techniques for modifying nucleotide sequences, such as sitedirected mutagenesis, are well known to those skilled in the art. See, e.g., T. Maniatis et al., supra; *DNA Cloning*, Vols. I and II, supra; *Nucleic Acid Hybridization*, supa.

A number of prokaryotic expression vectors are known in the art. See, e.g., U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pcDNA1neo, a vector derived from pcDNA1(*Mol. Cell Biol.* 7:4125–29) which uses the CMV promoter to drive expression. Both these latter two vectors can be employed for transient or stable(using G418 resistance) expression in mammalian cells. Insect cell expression systems, e.g., Drosphilia, are also useful, see for example PCT applications U.S. patent application Ser. No. 89/05155 and U.S. patent application Ser. No. 91/06838 as well as EP application 88/304093.3.

Depending on the expression system and host selected, the proteins of the present invention are produced by growing host cells transformed by an expression vector described above under conditions whereby the protein of interest is expressed. It is preferred to employ as a host a cell type that produced little or no endogenous PDE IV so as to make the identification and recovery of the recombinant form easier The protein is then isolated from the host cells and purified. If the expression system secretes the protein into growth media, the protein can be purified directly from the media. If the protein is not secreted, it is isolated from cell lysates or recovered from the cell membrane fraction. In certain cases were the protein is localized to the cell surface, whole cells or isolated membranes can be used as an assayable source of the desired gene product. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired enzyme.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides is not particularly preferred.

The proteins of the present invention or their fragments comprising at least one epitope can be used to produce antibodies, both polyclonal and monoclonal. If polyclonal antibodies are desired, a selected mammal, (e.g., mouse, rabbit, goat, horse, etc.) is immunized with a receptor of the present invention, or its fragment, or a mutated receptor. Serum from the immunized animal is collected and treated according to known procedures. If serum containing polyclonal antibodies is used, the polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980); see also (U.S. Pat. Nos. 4,341,761; 4,399,121; 4,427,783; 4,444,887; 4,452,570; 4,466,917; 4,472,500; 4,491,632 and 4,493,890. Panels of monoclonal antibodies produced against the antigen of interest, or fragment thereof, can be screened for various properties; i.e., for isotype, epitope, affinity, etc. Monoclonal antibodies are useful in purification, using immunoaffinity techniques, of the individual antigens which they are directed against. Alternatively, genes encoding the monoclonals of interest may be isolated from the hybridomas by PCR techniques known in the art and cloned and expressed in the appropriate vectors. The antibodies of this invention, whether polyclonal or monoclonal have additional utility in that they may be employed reagents in immunoassays, RIA, ELISA, and the like.

In other embodiments cell membrane fractions comprising the enzyme, partially purified supernatants containing the enzyme or isolated enzyme free or immobilized on solid supports may be used to measure binding of compounds to be tested. When recombinant cells are used for purposes of expression of the enzyme, it is preferred to use cells with little or no endogenous enzyme activity so that binding if any is due to the presence of the expressed enzyme of interest. Preferred cells include yeast cells, particularly those of *Saccharomyces cerevisiae* that have been engineered to lack endogenous PDE activity. In a further embodiment a specific localization of PDE $IV_B$ can be achieved. For example a fusion protein can be made by fusing the enzyme of this invention with a protein domain which directs incorporation of such a fusion into the cell wall or cell membrane of the host cell. Such a domain, referred to here as a cell surface localizing domain, is capable, itself, or in association with accessory signal sequences known in the art, of directing the expression of the fusion protein and its integration into the host cell membrane or cell wall. It is most preferable to integrate the fusion protein so that the PDE $IV_B$ domain is displayed on the external surface of the host cell.

In the compound screening embodiment of this invention, the enzyme partially purified or in isolated, immobilized or cell bound form is contacted with a plurality of candidate molecules and those candidates are selected which bind to and interact with the enzyme (e.g., enzyme inhibitors). The binding or interaction can be measured directly by using radioactively labeled candidate of interest.

Alternatively, the candidate compounds can be subjected to a competition screening assays, in which a known ligand (e.g., rolipram), preferably labeled with an analytically detectable reagent, most preferably radioactivity, is introduced with the compound to be tested and the compound's capacity to inhibit or enhance the binding of the labeled ligand is measured. Compounds are screened for their increased affinity and selectivity to the enzyme class of interest. In yet another approach advantage is taken of the catalytic activity of PDE $IV_B$. Specifically, since PDE $IV_B$ hydrolyzes the 3'-phosphoester bond of cyclic nucleotides (e.g., cyclic AMP) to form 5'-monophosphate products, candidate molecules can be screened for their ability to inhibit the hydrolysis of cyclic nucleotides labeled with the appropriate analytically detectable reagent(e.g., radioactive, fluorometric or colorimetric agent).

In yet another embodiment human PDE $IV_B$ finctionally expressed in host cells, especially yeast may be employed in a rapid, high-throughput screen to identify enyzme-selective inhibitors from sources such as natural. products. Cells of *Saccharomyces cerevisiae* contain two genes that encode endogenous cAMP PDEs (Sass, P. et al., *Proc. Nat'l. Acad. Sci. USA* 83:9303–07 (1986); Wilson, R. B. et al., Mol. Cell. Biol. 8:505–510 (1988) and Nikawa, J. I. et al., Mol. Cell. Biol. 7:3629–36 (1987)). PDE-deficient mutants were constructed by reverse genetic techniques (gene disruption) according to the method of Rothstein et al. (Cloning in Yeast. In: "DNA Cloning II: a practical approach", D. M. Glover ed., IRL Press, Washington D.C., pgs 45–66 (1990)) and were found to be viable, but to exhibit specific growth arrest phenotypes associated with elevated cAMP content. These phenotypes include: heat shock sensitivity, sensitivity to nitrogen starvation and the inability to grow on media containing suboptimal carbon sources such as acetate. The details for the agar plate assay (i.e., media composition and conditions for assaying growth arrested phenotype) are described in Sass et al. supra; Wilson et al., supra; Nikawa et al., supra and McHale, M. M. et al., *Mol. Pharm.* 39:109–113 (1991). Briefly, cells are grown in SC-Trp liquid medium for 2 days at 30° C., spotted onto SC-Trp agar medium containing 5 mM cAMP and 150 $\mu$M $CuSO_4$ and incubated for 2 days at 30° C. For heat shock, cells are replicated from the master plate onto two plates each containing the same medium as describe above, one of which is preheated to 55° C. for 1 hour. Cells transferred to the preheated plate are incubated at 55° C. for 5 minutes and then shifted to 30° C. For monitoring growth on acetate, the master plate is replicated to a plate containing the same medium except 2% potassium acetate instead of glucose. Growth is scored after five days at 5 days at 30° C.

Functional expression of human PDE $IV_A$ or PDE $IV_B$ in genetically engineered PDE-deficient strains of *S. cerevisiae* reverses the aberrant phenotypes described above. Furthermore, under conditions for growth arrest, rolipram, as well as certain other selective mammalian PDE IV inhibitors, are cytotoxic to PDE-deficient mutant cells expressing the human PDE IV under growth arrest conditions. At the same time, rolipram has no killing effect on either wild-type yeast cells or on PDE-deficient cells expressing the human PDE IVs under normal growth conditions. These controls indicate that rolipran is not simply acting as an antifungal agent. Instead, it is entering the yeast cells and inhibiting the activity of the human recombinant enzyme in the cells; this, in turn, results in an elevation of cAMP content and an unmasking of the concomitant growth arrest phenotype.

Such a system provides the basis for a high throughput screen for PDE IV subtype-specific inhibitors. The source of compound for screening includes pure chemicals as well as natural products (e.g., fermentation broths from soil microorganisms, extracts from plants, animals and marine microorganisms). In such a screen, compounds are identified by the ability to kill cells incubated under the prescribed conditions for growth arrest (where cell viability depends on the functional expression (biological activity) of the human recombinant PDE IV) but at the same time, not affect wild-type cells. Although yeast cells may possess certain barriers (i.e., cell wall) that may make them less sensitive than mammalian cells to certain small molecules, such shortcomings are readily overcome by increasing the permeability of the yeast cell by for example, mutating genes that effect the synthesis of cell membrane components (e.g., ergosterol) See for example, Gaber, R. F., et al., *Mol. Cell. Biol.* 9:3447–3456 (1989).

This system also offers an excellent method for rapidly assaying genetically engineered site specific mutants of human PDE $IV_B$ for functional catalytic activity in cells. Furthermore, this system allows for the direct selection of rolipram-resistant and catalytically active mutants of PDE IV which when characterized in terms of DNA sequence may reveal amino acid residues involved in compound binding.

New compounds found to specifically inhibit the recombinant enzyme in vitro (see above) are then compared to rolipram or other reference compounds with respect to their capacity to unmask the inherent growth arrest phenotypes present in the yeast screening strains under appropriate culture conditions. In addition PDE IV inhibitors identified in natural products can be chemically purified and assayed for the ability to inhibit the recombinant enzyme(s) in vitro.

In yet another aspect of this invention, the discovery of the heretofore unknown human PDE $IV_B$ subtype provides a new method for rapidly screening subtype-specific inhibitors. Accordingly, the PDE IV A and B subtypes are expressed in separate PDE-deficient yeast strains and candidate compounds are screened for their ability to inhibit one but not both the enzyme subtypes. Thus compounds may be identified that inhibit the monocyte A form but not the brain B form of PDE IV.

This invention also contemplates pharmaceutical compositions comprising compounds when identified by the above methods and a pharmaceutically acceptable carrier. Pharmaceutical compositions of proteineous drugs of this invention are particularly useful for parenteral administration, i.e., subcutaneously, intramuscularly or intravenously. The compositions for parenteral administration will commonly comprise a solution of the compounds of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques. The compositions may contain pharmaceutically acceptable auxiliary substances as required to approximate physiological conditions such as pH adjusting and buffering agents, etc. The concentration of the compound of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 ml sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, *Remington's Pharmaceutical Science*, 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

In situations where the identified compound is non-proteineous, it may be administered alone or in combination with pharmaceutically acceptable carriers, the proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered sublingually in the form of troches or lozenges in which the active ingredient is mixed with sugar and corn syrups, flavoring agents and dyes; and then dehydrated sufficiently to make it suitable for pressing into a solid for. They may be administered orally in the form of solutions which may be injected parenterally, that is, intramuscularly, intravenously or subcutaneously. For parenteral administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenteally. The compounds are useful in the same manner as other PDE $IV_B$-effecting agents and the dosage level is of the same order of magnitude as is generally employed with these other therapeutic agents. The therapeutic dosage will generally be fiom 1 to 10 milligrams per day and higher although it may be administered in several different dosage units. Tablets containing from 0.5 to 10 mg. of active agent are particularly useful.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the compounds of the invention sufficient to effectively treat the patient.

The nucleic acid embodiment of this invention is particularly useful in providing probes capable of specific hybridization with human PDE $IV_B$ sequences. Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. This invention contemplates, for example using PDE $IV_B$ encoding probes in the diagnostic evaluation of disease states characterized by an abnormal, i.e., increased or decreased level of PDE $IV_B$ gene expression. Alternatively, the probes can be used to identify individuals carrying chromosomal or molecular mutations in the gene encoding the enzyme. Depending on the conditions employed by the ordinary skilled artisan, the probes can be used to identify and recover additional examples of the PDE $IV_B$ enzyme from other cell types and individuals. As a general rule the more stringent the hybridization conditions the more closely related genes will be that are recovered.

Also within the scope of this invention are antisense oligonucleotides predicated upon the sequences disclosed herein for. the PDE $IV_B$ enzyme. Synthetic oligonucleotides or related antisense chemical structural analogs are designed to recognize and specifically bind to a target nucleic acid encoding the receptor gene and inhibit gene expression, e.g., the translation of the gene when the target nucleic acid is mRNA. Although not wishing to be bound to a particular theory for the mechanism of action of antisense drugs, it is believed that such drugs can act by one or more of the following mechanisms: by binding to mRNA and inducing degradation by endogenous nucleases such as RNase I or by inhibiting the translation of mRNA by binding to regulatory factors or ribosomal components necessary for productive protein synthesis. Additionally the antisense sequences can be used as components of a complex macromolecular arrays in which the sequences are combined with ribozyme sequences or reactive chemical groups and are used to specifically target mRNAs of interest and degrade or chemically modify said mRNAs. The general field of antisense technology is illustrated by the following disclosures which are incorporated herein by reference for purposes of background (Cohen, J. S., *Trends in Pharm. Sci.* 10:435(1989) and Weintraub, H. M. *Scientific American* January (1990) at page 40).

This invention also contemplates antibodies, monoclonal or polyclonal directed to epitopes corresponding to amino acid sequences disclosed herein from the PDE $IV_B$ enzyme. Particularly important regions of the enzyme for immunological purposes are those catalytic and allosteric domains of the enzyme. Antibodies or fragments thereof directed to these regions are particularly useful in diagnostic and therapeutic applications because of their effect upon enzyme-ligand interaction. Methods for the production of polyclonal and monoclonal antibodies are well known, see for example Chap. 11 of Ausubel et al. (supra).

This invention also provides pharmaceutical compositions comprising an effective amount of antibody or antigen binding fragments thereof directed against the PDE $IV_B$ enzyme to block binding of naturally occurring ligands to that enzyme in order to treat or ameliorate disease states associated with inappropriate enzyme activation. In its diagnostic embodiment the PDE $IV_B$ enzyme can be detected by contacting it with antibodies of this invention and measuring the antibody/enzyme complex. When the antibody is labeled with an analytically detectable reagent such a radioactivity, fluorescence, or an enzyme, the antibody can be use to detect the presence or absence of the enzyme and/or its quantitative level.

As disclosed herein below, screening a human frontal cortex library revealed the existence of a unique cDNA that encodes a protein with 76% amino acid sequence identity to hPDE $IV_A$. Expression of this cDNA in PDE-deficient yeast cells indicates that the gene product possesses characteristics consistent with those of the PDE IV enzyme family. Specifically, the recombinant enzyme, designated hPDE $IV_B$, has a cAMP $K_m=4$ $\mu$M and exhibits very poor activity with cGMP as a substrate. Moreover, the activity of this enzyme is inhibited by rolipram ($K_i=0.085$ $\mu$M) and other PDE IV-selective inhibitors, but not by compounds that selectively inhibit other PDE isozymes. Similar to the results obtained with hPDE $IV_A$, rolipram does not inhibit hPDE $IV_B$ activity in a purely competitive fashion. While not wishing to be bound by any particular explanation, this could reflect a kinetically complex mechanism of inhibition by rolipram (e.g., allosteric interaction) or could indicate that the recombinant hPDE $IV_B$ exists in two distinct, catalytically active, non-interconvertable forms, both of which can be inhibited competitively by rolipram but with significantly different $K_i$s. Based upon the limited evaluation of hPDE $IV_B$ carried out thus far, it appears that the kinetic properties of this subtype are similar to hPDE $IV_A$.

As observed with hPDE $IV_A$, hPDE $IV_B$ catalytic activity and high affinity rolipram binding are coexpressed. Thus, high affinity rolipram binding is a property of both hPDE $IV_A$ and hPDE $IV_B$. Interestingly, at least two classes of kinetically distinct high affinity rolipram-binding sites exist on hPDE $IV_B$ ($K_d$s=0.4 and 6 nM), whereas only one class ($K_d=2$ nM) is present on hPDE $IV_A$.

Valuable information regarding enzyme structure and function can obtained from comparisons of the predicted primary amino acid sequences of different PDEs. All of the well-studied mammalian PDEs exhibit a common structure consisting of a highly conserved 270–300 amino acid sequence within the central core of the molecule corresponding to the catalytic domain, flanked by variable N-terminal and C-terminal extensions. Based on a considerable amount of biochemical data, the conserved region contains the information for catalytic activity, whereas the nonconserved regions may dictate subtype-specificity in terms of regulation of enzymatic activity, cellular distribution or subcellular localization. Alignment of the primary amino acid sequence of hPDE $IV_B$ with that of one of the rat brain enzymes (rPDE $IV_B$ in FIGS. 2A, 2B, and 2C) shows that they are nearly identical (from residues 38 to 564); this conservation of sequence includes the C-terminal end of each molecule. In contrast, comparison of the hPDE $IV_A$ and hPDE $IV_B$ subtypes reveals striking sequence divergence, especially at the N-terminal and C-terminal ends. This suggests that there is a greater degree of sequence conservation between the "same" isozyme subtype from different species than among "different" subtypes from the same species.

Although significant structural similarity in the conserved regions was observed between hPDE $IV_A$ (which is known to be expressed in human monocytes), and one of the enzymes cloned from a rat brain cDNA library (rPDE $IV_A$ in FIGS. 2A, 2B, and 2C), it is impossible to draw a conclusion regarding the functional relationship between these two subtypes considering the extensive sequence divergence present at their N-terminal and C-terminal ends. The prominent characteristic that separates these two subtypes from the others, however, is the long C-terminal domain. It is quite possible the two subtypes are functionally equivalent, and that the rat brain enzyme is not really brain-specific. That is, the mRNA template for the rat brain cDNA could actually have come from contaminating blood monocytes. Unfortunately, the analysis of the tissue-distribution of the rat PDE IV transcripts, which showed expression in all tissues examined, used full-length cDNAs as probes and therefore did not differentiate the expression of various subtypes (Swinnen, J. V. et al., *Proc. Natl. Acad. Sci. USA* 86:5325–5329 (1989)).

Using a DNA probe consisting of nonconserved sequences, the human tissue distribution of hPDE $IV_B$ mRNA was analyzed herein and found to exhibit a restricted pattern of expression. An ~4-kb message was easily detected in brain, as well as in three other tissues, but not in placenta, liver, kidney and pancreas. In brain, we observed an additional ~5-kb mRNA species which may represent unprocessed mRNA. Alternatively, the identification of two hPDE $IV_B$-related mRNAs in brain tissue may correspond to differentially spliced transcripts expressed from the same gene, or instead, may indicate the presence of another as yet unidentified gene.

More important is the differential response of hPDE $IV_A$ and hPDE $IV_B$ to inhibitors. Predicated upon such a response, subtype specific drug screening can be developed. In one embodiment of this invention a screening protocol may be conducted as outlined hereinabove.

EXAMPLE 1

This example provides the details of the cloning, expressing and characterization of the PDE $IV_B$ of this invention.

Experimental Procedures

Isolation of cDNA—A commercially prepared human frontal cortex cDNA library constructed in λZAP (Stratagene; average insert size—1.5 kb) was screened with a $^{32}$P-labeled (random-primed; Pharmacia) 1.8-kb SmaI fragment of the human monocyte cDNA clone hm-PDE1 (formerly hPDE-1) which encodes a PDE IV. Hybridizations were carried out at 65° C. in 6×SCP (0.6 M NaCl, 0.81 M $Na_2HPO_4$, 6 mM EDTA, pH 6.2), 10% dextran sulfate, 5×Denhardt's (0.01% ficoll, 0.01% polyvinylpyrrolidone, 0.01% bovine serum albumin), 0.1% SDS and 100 mg/ml salmon sperm DNA. Filters were washed in 2×SCP, 0.1% SDS at 65° C. and autoradiographed. A number of clones were isolated and partially characterized by restriction mapping. DNA sequencing of one 2.7-kb clone (hb-PDE1a) by the method of Sanger, F. et al. (*Proc. Natl. Acad. Sci. USA* 74:5463–67 (1977)) revealed that it contained a truncated ORF, predicting a protein with homology to only the 3' half of PDE protein encoded by hm-PDE1. A 0.69-kb NdeI-SphI fragment, containing the majority of the ORF of clone hb-PDE1a was then used to screen a custom cDNA library prepared at Stratagene from human frontal cortex tissue (also in λZAP). This library was prepared using methods to insure large insert sizes. Briefly, the RNA was denatured in the presence of methyl mercury and converted to cDNA using 80% oligo dT and 20% random priming. The cDNA was then size-selected for inserts of 1.5-kb and greater by agarose gel electrophoresis. Labeling, hybridization and washing conditions were identical to those stated above. This screen yielded 11 clones which were analyzed by restriction mapping. The DNA sequence of the largest clone, hb-PDE1, was determined and found to overlap the sequence of hb-PDE1a by 1.35 kb, and extend 1.28 kb further upstream (5'); the total size of hb-PDE1 is 2.63 kb. Thus, the composite of hb-PDE1a and hb-PDE1 represent a cDNA containing both 5' and 3' UTRs. hb-PDE1 alone encodes a full-length PDE IV-related protein (called hPDE $IV_B$) as judged by an alignment of its primary amino acid sequence with that of other PDE IV subtypes (see FIGS. 2A, 2B, and 2C).

Northern Analysis—An "hb-PDE1-specific" DNA probe was generated by PCR (see: Mullis, K. B. and F. A. Faloona, *Meth of Enz.* 155:335–50 (1987)) using the following oligonucleotide primers: 5'-GGGG<u>CTCGAG</u>GAGGGACA CACGTATTTCAGCAGCACAAAG-3' (Seq. ID No:3)and 3'-CTCACTTGAGTGACTGATTATTGAAGTAAA <u>GAGCTG</u>GGG-5'.(Seq. ID No:4) This fragment was subcloned into pGEM7 (Promega) using the unique XhoIsites (underlined). The XhoI fragment was gel purified, $^{32}$P-labeled (random-primed; Pharmacia), and hybridized to a Northern blot containing poly (A)$^+$ RNA extracted from multiple human tissues (Clonetech); hybridization conditions were: 42° C. in 5×SSPE (0.75M NaCl, 0.2 M $NaH_2PO_4.H_2O$, 5 mM $Na_2EDTA$, pH7.4), 10×Denhardt's, 100 mg/ml salmon sperm DNA, 50% formamide and 2% SDS. The blot was washed in 0.1×SSC (15 mM NaCl, 1.5 mM sodium citrate, pH7.0), 0.1% SDS at 50° C. and autoradiographed. The same blot was stripped with boiling water and reprobed with a 2-kb human mactin-encoding cDNA (see: Cleveland, D. W. et al. *Cell* 20:95–105 (1980)). Labeling, hybridization and washing conditions were the same as above.

Expression of hPDE $IV_B$ in *Saccharomyces cerevisiae*— The hb-PDE1 cDNA was engineered for expression in yeast as follows: the 2.08-kb XhoI (5' polylinker)-NcoI fragment of pBluescript/hb-PDE1 was subcloned into the unique XhoI and NcoI polylinker sites of the yeast expression plasmid p138NB (McHale, M. M. et al. *Mol. Pharmacol.* 39:109–113 (1991)). The 5' UTR of hb-PDE1 was then deleted by removing the 1.1-kb XhoI-PvuII fragment and replacing it with a 0.79-kb XhoI-PvuII hb-PDE1 fragment generated by PCR in which a XhoI site was engineered just upstream of the initiating methionine codon. The oligonucleotide primers used for PCR were: 5'-GGG GG<u>CTCGAG</u>AATGAAGGAGCACGGGGGCA C C T T C AGTAGC-3' (Seq. ID No:5)and 3'-GACGGTAAA A A C GT<u>CGAC</u>GGTAGGCTACGC-5'(Seq. ID No:6). The PCR-generated portion of this plasmid (p138NB/hb-PDE1) was sequenced and found to contain one base pair change that did not affect the amino acid sequence.

p138NB/hb-PDE1 contains the TRP1 selectable marker and partial 2μ sequences for maintenance at high copy number, with hb-PDE1 expression driven by the copper inducible CUP1 gene promoter. The plasmid was introduced into the PDE-deficient *S. cerevisiae* strain GL62 (isogenic to strain GL61; described in McHale et al. (supra) (1991)) using the lithium acetate method (Ito, H., et al., *J. Bacteriol.* 153:163–168 (1983)). Trp+ prototroph were isolated and grown aerobically at 30° C. to an $A_{540}$=1.0 in synthetic complete medium lacking tryptophan. PDE expression was induced by the addition of 150 µM $CuSO_4$. Cells were harvested at 6 hr and 100,000×g supernatants were prepared as previously described by McHale et al. (supra).

PDE Assays and Inhibitor Studies—PDE activity was determined in 100,000×g supernatant fractions of yeast cell lysates. Briefly, the reaction was initiated by the addition of an aliquot of the yeast supernatant fraction to 0.1 ml (final volume) of a reaction mixture containing (final concentrations) 50 mM Tris-HCl (pH 7.5), 5 mM $MgCl_2$, 1 µM [$^3$H] cAMP (2000 dpm/pmol) and 0.05% BSA. To determine recovery, 50 µM 5'-[$^{14}$C] AMP (400 dpm/nmol) was added to each assay tube after the reaction was terminated. For studies in which the $IC_{50}$s of various inhibitors were determined, compounds were present in the reaction mixture at concentrations that varied over three orders of magnitude. Reactions were conducted at 30° C. for 30 min. The reactions were terminated, 5'-adenosine monophosphate was isolated, and PDE activity was determined as previously described (Torphy, T. J. and L. B. Cieslinski, *Mol. Pharmacol.* 37:206–214 (1990)). All assays were conducted in the linear range of reaction within which no greater than 10% of the initial substrate is hydrolyzed. cGMP hydrolysis was also assayed as described by Torphy, T. J. and Cieslinski (supra). Protein concentrations were determined as previously described (Lowry, O. H. et al. *J. Biol. Chem.* 193:265–75 (1951)).

Rolipram Binding Assay—[$^3$H] R-Rolipram binding was assessed by modification of the method of Schneider and co-workers (*Eur. J. Pharmacol.* 127:105–115 (1986)). For competition binding experiments, the reaction was conducted at 30° C. in 0.5 ml of a standard reaction mixture containing (final concentrations): 50 mM Tris-HCl (pH7.5), 5 mM $MgCl_2$, 50 µM 5'-AMP, 2 nM [$^3$H] R-rolipram (5.7×10$^4$ dpm/pmol) and 0.05% BSA. For saturation binding experiments, the concentration of [$^3$H] R-rolipram was varied from 0.02–24 nM. Nonspecific binding was defined in the presence of 1 µM unlabeled rolipram and was consistently less than 5% of total binding. The reaction was stopped after 1 h by the addition of 1 ml ice-cold reaction buffer (without [$^3$H] R-rolipram) and rapid vacuum filtration (Brandel Cell Harvester) through Whatman GF/B filters that had been soaked in 0.3% polyethylenimine. The filters were washed with an additional 5 ml of cold buffer, dried and counted via liquid scintillation spectrometry.

Determination of Kinetic and Binding Parameters—For determination of $V_{max}$, $K_m$, and $K_i$, the concentration of cAMP or cGMP was varied while the amount of $^3$H-labeled cyclic nucleotide per assay was kept constant. Appropriate corrections were made for the changes in specific activity of the substrate. Kinetics were analyzed with a KINPAC computer program described by W. W. Cleland (*Meth. of Enzymol.* 63:103–38 (1979)), using a nonlinear least-squares regression analysis. Analysis of [$^3$H] R-rolipram binding experiments, including determination of multiple $K_d$ and $V_{max}$ values, was carried out using the Acufit computer program (Beckman Instruments, Fullerton, Calif.). Statistical comparisons between one-site and two-site fits were conducted via F test.

Inhibitors and radioligand—R- and (S)-rolipram were synthesized by Dr. Sigfried Christensen and colleagues (SmithKline Beecham Pharmaceuticals, King of Prussia, Pa.); [$^3$H] R-rolipram (5.7×10$^4$ dpm/pmol) was prepared by Dr. Richard Heys and colleagues (SmithKline Beecham Pharmaceuticals, King of Prussia, Pa.); denbufylline was obtained from SmithKline Beecham Pharmaceuticals (Epsom, United Kingdom); Ro 20–1724 was purchased from BioMol (Plymouth Meeting, Pa.); zaprinast and siguazodan (SK&F 94836) were synthesized by Dr. William Coates and colleagues (SmithKline Beecham Pharmaceuticals, Welwyn, United Kingdom).

RESULTS

Cloning and Nucleotide Sequence of a Human Brain PDE IV cDNA—A DNA fragment from the conserved region of a human monocyte cDNA shown to encode a low-$K_m$ cAMP-specific PDE was used to probe a human frontal cortex cDNA library. Numerous clones were obtained, characterized by restriction mapping, and the DNA sequence of one 2.7-kb clone was determined. This clone (hb-PDE1a) contained sequence information which was homologous to a large 3' portion of the hPDE $IV_A$ cDNA. hb-PDE1a was then used to probe a second cDNA library which was custom synthesized fiom human frontal cortex. Again, numerous clones were obtained, and based on restriction analysis we determined the DNA sequence of one clone containing the longest 5' extension. FIGS. 1A, 1B, and 1C show the composite nucleotide sequence of these two cDNAs. hb-PDE1 extends from positions -283 to 2363, whereas hb-PDE1a extends from positions 1008 to 3609. The sequence contains an ORF of 1692 bp in length, which predicts a 564 amino acid protein with a calculated molecular mass of 64,202 (minus the N-terminal methionine). The ORF is flanked by 5' and 3' untranslated sequences of 283 and 1907 bp, respectively. The 3' UTR contains a putative polyadenylation signal (5'-AATAAA-3') at position 3572, followed by a poly (A) tract.

Analysis of the Predicted hb-PDE1 Protein Sequence—FIGS. 2A, 2B, and 2C show an alignment of the hPDE $IV_B$ primary amino acid sequence with the sequences of three other cloned mammalian PDE IVs, one from human monocytes (hPDE $IV_A$), and two from rat brain (rPDE $IV_A$; rPDE $IV_B$). Recombinant forms of all of these other enzymes have been found to exhibit the biochemical properties indicative of a type IV PDE. There is striking homology between the hPDE $IV_B$ protein and all of the other PDE IVs, especially within the central core of the molecule which has been proposed to contain the catalytic domain. Interestingly, the sequence of hPDE IVB is significantly more homologous to the sequence of one of the rat brain proteins (rPDE $IV_B$; 92% identity over 562 amino acids; 98% identity over 526 amino acids starting at residue 38 of hPDE $IV_B$) than to the PDE IV from human monocytes (hPDE $IV_A$; 76% identity over 538 amino acids) (FIGS. 2A, 2B, and 2C). In fact, the protein sequences of hPDE $IV_B$ and rPDE $IV_B$ precisely align at their C-terminal ends. The relationship between these two proteins is made even more apparent by the perfect alignment of sequence gaps inserted to accurately compare all four proteins (FIGS. 2A, 2B, and 2C). It is also quite apparent that, whereas hPDE $IV_B$ and rPDE $IV_B$ are highly homologous to one another, the sequence of the hPDE $IV_A$ protein is very similar to that of the other rat brain protein, rPDE $IV_A$ (83% identity over 504 amino acids). Both hPDE $IV_A$ and rPDE $IV_A$ contain an insertion near the N-terminal end (adjacent to residue 131 of hPDE $IV_B$) and a long C-terminal extensions not found on the other two proteins. FIGS. 2A, 2B, and 2C also shows that many of the differences between the hPDE $IV_B$ and both the hPDE $IV_A$ and rPDE $IV_A$ involve residues that are conserved among the latter two proteins. Thus, there is a lesser degree of protein sequence conservation between the two human PDE IVs than between two PDE IVs derived from the brain tissues from different species.

Expression of hPDE $IV_B$ in Yeast and Evaluation of its Catalytic Activity—In order to biochemically characterize the recombinant hPDE $IV_B$ enzyme, the hb-PDE1 cDNA was engineered for overexpression in the yeast *S. cerevisiae*.

This was done using a genetically-engineered PDE-deficient strain of yeast which contained genomic disruptions of the two genes encoding endogenous cAMP-specific PDEs.

Figures 2, 3A:
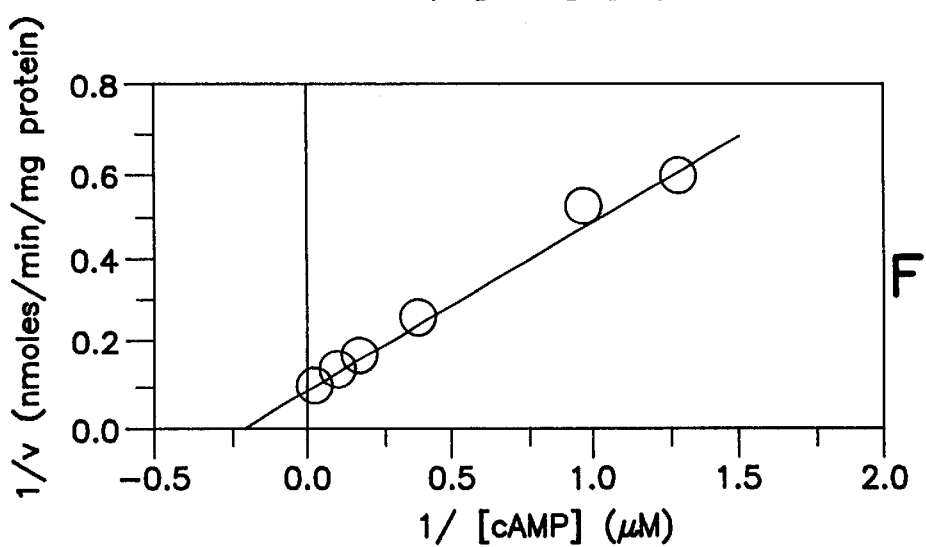
Figure 3B:
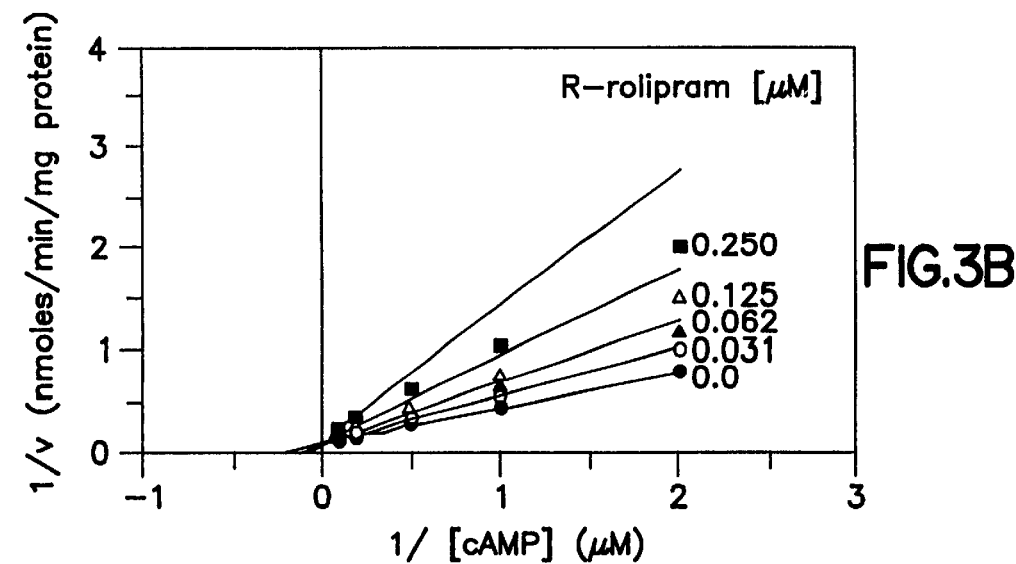
FIG. 3B, analysis of the inhibitory effect of R-rolipram on cAMP hydrolysis by hPDE IV$_B$. The symbols represent the actual experimental data whereas the lines were generated from the KINPAC kinetic analysis program and represent the theoretical position of data points for a competitive inhibitor with a K$_i$=0.085 μM.

Soluble fractions of yeast cells containing an expression plasmid for hPDE $IV_B$ (p138NB/hb-PDE1) accumulated an appreciable amount of cAMP hydrolyzing activity following induction (2.0 nmol/min per mg of protein in the presence of 1μ M[$^3$H]cAMP), compared to a negligible amount of activity seen in samples from cells containing plasmid lacking the cDNA insert (p138NB). The hPDE IV activity expressed in yeast exhibited standard Michaelis-Menton behavior with respect to catalytic activity and a high affinity for cAMP, with a $K_m$ of 4.3 μM and a $V_{max}$=11.3 nmol/mg protein/min (FIGS. 3A–1 and 3A–2). Furthermore, R-rolipram potently inhibited catalytic activity ($K_i$=0.085 μM), although the inhibition observed did not appear to be strictly competitive (FIG. 3B). The recombinant enzyme was also inhibited by two other PDE IV inhibitors, Ro 20–1724 ($IC_{50}$=2.2 μM) and denbufylline ($IC_{50}$=0.5 μM), but not by siquazodan or zaprinast ($IC_{50}$s>30 μM), inhibitors of PDE III and PDE V, respectively. No detectable hydrolysis of cGMP was noted, even at substrate concentrations as great as 10 mM.

Figure 4:
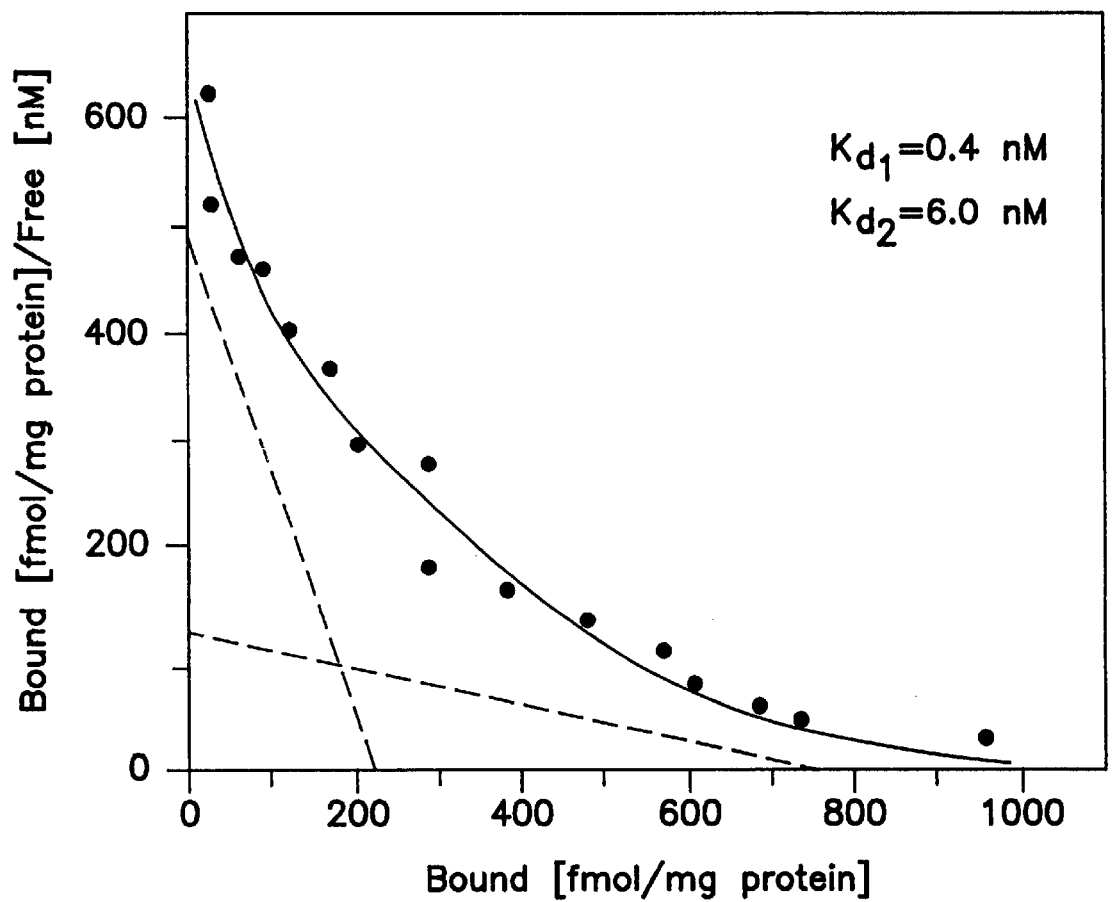
FIG. 4 illustrates Scatchard analysis of [$^3$H] R-rolipram binding. Supernatant fractions of yeast cell lysates prepared 6 hr after induction of hPDE IV$_B$ expression were incubated with various concentrations of [$^3$H] R-rolipramn (0.02–24 nM). Assays were conducted in the presence or absence of 1 μM unlabeled rolipram to define saturable binding. The results shown represent a Scatchard analysis of saturable [$^3$H] R-rolipram binding, which corresponded to more than 95% of the total binding. As analyzed by the Acufit computer program, the data best fitted a two-site model (F<0.01) with rolipram K$_d$s=0.4 and 6 nM. The data are representative of the results obtained with two preparations.

[$^3$H] R-rolipram Binding—A typical Scatchard analysis of saturation binding experiments with [$^3$H] R-rolipram is shown in FIG. 4. The Scatchard plots were consistently curvilinear and best fitted a two-site model rather than a one-site model (F<0.01). Assuming that the curvilinear Scatchard plots reflected two distinct binding sites rather than a negatively cooperative interaction, $K_d$s of 0.4 nM and 6 nM were calculated with the higher affinity sites representing approximately one-third of the total sites.

A comparison of the kinetic behavior and [$^3$H] rolipram-binding characteristics of hPDE $IV_A$ and hPDE $IV_B$ is shown in Table 1. The kinetic characteristics of these subtypes are virtually identical with respect to their catalytic activity against cAMP and cGMP, as well as their sensitivity to R-rolipram. However, unlike hPDE $IV_B$, which appears to contain more than one high affinity rolipram-binding site (FIG. 4), hPDE $IV_A$ possesses only a single class of noninteracting high affinity binding sites.

TABLE I

Comparison of the kinetic behavior and [$^3$H] R-rolipram binding characteristics of hPDE $IV_A$ and hPDE $IV_B$

| Subtype | $K_m$ cAMP μM | $K_m$ cGMP μM | R-Rolipram $K_i$ nM | [$^3$H] R-Rolipram $K_d$ nM |
|---|---|---|---|---|
| hPDE $IV_A$[a] | 3.1 | >100 | 60 | 1 |
| hPDE $IV_B$ | 4.3 | >10,000 | 85 | 0.4, 6 |

Figure 5A:
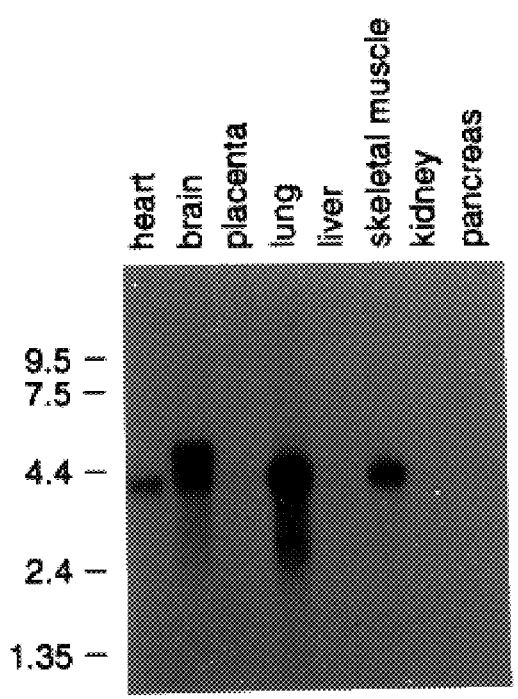
FIGS. 5A and 5B illustrate the human tissue distribution of hb-PDE1-specific mRNA. A Northern blot containing poly (A)$^+$ mRNA extracted from various human tissues was probed with a $^{32}$P-labeled PCR fragment of hb-PDE1 corresponding to a nonconserved 3' region (see FIGS. 1A, 1B, and 1C) in Panel A, stripped, and reprobed with a 32P-labeled β-actin cDNA in Panel B. Each lane contained 2 μg of poly (A)$^+$ RNA from the indicated human tissue. Size markers are in kb.
Figure 5B:
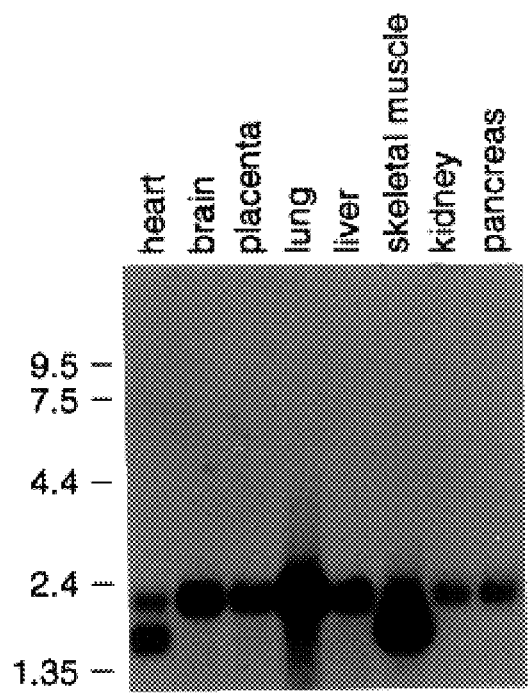

[a]Data from Torphy, T.J. et. al., J. Biol. Chem. 267: 1798–1804 (1992).

mRNA Tissue Distribution—mRNA transcripts corresponding to hb-PDE1 were detected in only half of the human tissues surveyed (FIG. 5A). Northern blot analysis of poly (A)$^+$ RNA derived from various human tissues revealed the presence of an ~4-kb mRNA in brain, heart, lung and skeletal muscle, with no mRNA detected in placenta, liver, kidney and pancreas. An additional ~5-kb mRNA was detected in brain, present in approximately equal abundance relative to the ~4-kb mRNA (FIG. 5A). For these studies, a probe which consisted of an hb-PDE1 fragment representing a nonconserved portion of the coding region plus a portion of the 3' UTR (underlined sequence in FIGS. 1A, 1B, and 1C) was used. The blot was stripped and reprobed with a 2-kb human β-actin cDNA as a control for the presence of RNA in each lane. FIG. 5B show that the amount of poly (A)$^+$ RNA loaded from each tissue was roughly equivalent, with the exception of lung which was apparently overloaded; the lower ~1.8-kb β-actin band observed in heart and skeletal muscle represents a second muscle-specific form of the protein.

What is claimed is:

1. A method for identifying at least one ligand that binds to a polypeptide comprising the amino acid sequence of SEQ ID NO: 2, wherein said method comprises the steps of:
    (a) contacting a polypeptide comprising the amino acid sequence of SEQ ID NO: 2 with at least one candidate ligand labeled with a detectable reagent; and
    (b) determining whether said ligand binds said polypeptide.

2. The method of claim 1, wherein said compound is radioactively or fluorescently labeled.

3. A screening method, comprising the steps of:
    (a) contacting a polypeptide comprising the amino acid sequence of SEQ ID NO: 2 with at least one candidate compound in the presence of a detectable ligand known to bind said polypeptide under conditions that permit binding of said compound and said ligand with said polypeptide; and
    (b) determining whether said compound enhances or inhibits the binding or interaction of said ligand with said polypeptide.

4. The method of claim 3, wherein said ligand is selected from the group consisting of rolipram, a rolipram derivative, a rolipram mimetic, cAMP, a cAMP mimetic and a cAMP derivative.

5. The method of claim 4, wherein said ligand is radioactively or flourescently labeled.

6. The method of claim 3, wherein said ligand is $^3$H-cAMP or $^3$H-cAMP derivative, and said determining step detects catalytic conversion of said ligand.

7. A screening assay, comprising the steps of:
    (a) providing a substantially phosphodiesterase deficient host cell that exhibits a specific growth arrest phenotype associated with elevated cAMP levels;
    (b) introducing a plasmid into said host cell, said plasmid comprising a nucleic acid molecule comprising a nucleic acid sequence encoding a polypeptide comprising a polypeptide of SEQ ID NO: 2;
    (c) culturing said host cell under conditions sufficient to express said polypeptide and sufficient to generate a growth arrest response should said expressed polypeptide be inhibited;
    (d) contacting said host cell with at least one candidate compound; and
    (e) identifying at least one compound that inhibits or enhances said polypeptide, thereby discovering said growth arrest phenotype.

8. The method of claim 7, wherein said host cell is a yeast cell and said plasmid is p138NB/hb-PDE1.

9. The method of claim 7, wherein said specific growth arrest phenotype is selected from the group consisting of sensitivity to nitrogen starvation, heat shock sensitivity, and inability to grow on suboptimal carbon sources.

10. A screening assay, comprising the steps of:
    (a) providing a substantially phosphodiesterase deficient host cell;
    (b) introducing a polynucleotide into said host cell, said polypeptide comprising a nucleic acid sequence encoding a polypeptide comprising the polypeptide of SEQ ID NO: 2;
    (c) contacting said host cell with at least one candidate compound; and
    (d) determining whether said compound inhibits said polypeptide comprising the polypeptide of SEQ ID NO: 2.

* * * * *

UNITED STATES PATENT AND TRADEMARK OFFICE
CERTIFICATE OF CORRECTION

| | | |
|---|---|---|
| PATENT NO. | : 6,306,583 B1 | Page 1 of 1 |
| DATED | : October 23, 2001 | |
| INVENTOR(S) | : George P. Livi, Megan M. McLaughlin and Theordore J. Trophy | |

It is certified that error appears in the above-identified patent and that said Letters Patent is hereby corrected as shown below:

<u>Column 31,</u>
Line 60, delete "flourescently" and insert therefor -- fluorescently --.

Signed and Sealed this

Twenty-third Day of April, 2002

*Attest:*

JAMES E. ROGAN
*Attesting Officer*     *Director of the United States Patent and Trademark Office*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 3890 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Homo sapiens
      (F) TISSUE TYPE: Brain (ix) FEATURE:
      (A) NAME/KEY: CDS
      (B) LOCATION: 282..1973

(xi) SEQUENCE DESCRIPTION: SEQ ID NO:1:

```
GGCACGAGCC TAAAGAACCT CGGGATGACT AAGGCAGAGA GAGTCTGAGA AAACTCTTTG     60
```

-continued

```
GTGCTTCTGC CTTTAGTTTT AGGACACATT TATGCAGATG AGCTTATAAG AGACGCTTCC     120

CTCCGCCTTC TTCCTCAGAG GAAGTTTCTT GGTAGATCAG GCACACCTCA TCCAGGCGGG     180

GGGTTGGGGG GAAACTTGGC ACCAGCCATC CCAGGCAGAG CACCACTGTG ATTTGTTCTC     240

CTGGTGGAGA GAGCTGGAAG GAAGGAGCCA GCGTGCAAAT A ATG AAG GAG CAC         293
                                             Met Lys Glu His
                                              1

GGG GGC ACC TTC AGT AGC ACC GGA ATC AGC GGT GGT AGC GGT GAC TCT       341
Gly Gly Thr Phe Ser Ser Thr Gly Ile Ser Gly Gly Ser Gly Asp Ser
  5              10                  15                  20

GCT ATG GAC AGC CTG CAG CCG CTC CAG CCT AAC TAC ATG CCT GTG TGT       389
Ala Met Asp Ser Leu Gln Pro Leu Gln Pro Asn Tyr Met Pro Val Cys
              25                  30                  35

TTG TTT GCA GAA GAA TCT TAT CAA AAA TTA GCA ATG GAA ACG CTG GAG       437
Leu Phe Ala Glu Glu Ser Tyr Gln Lys Leu Ala Met Glu Thr Leu Glu
              40                  45                  50

GAA TTA GAC TGG TGT TTA GAC CAG CTA GAG ACC ATA CAG ACC TAC CGG       485
Glu Leu Asp Trp Cys Leu Asp Gln Leu Glu Thr Ile Gln Thr Tyr Arg
          55                  60                  65

TCT GTC AGT GAG ATG GCT TCT AAC AAG TTC AAA AGA ATG CTG AAC CGG       533
Ser Val Ser Glu Met Ala Ser Asn Lys Phe Lys Arg Met Leu Asn Arg
 70                  75                  80

GAG CTG ACA CAC CTC TCA GAG ATG AGC CGA TCA GGG AAC CAG GTG TCT       581
Glu Leu Thr His Leu Ser Glu Met Ser Arg Ser Gly Asn Gln Val Ser
 85                  90                  95                 100

GAA TAC ATT TCA AAT ACT TTC TTA GAC AAG CAG AAT GAT GTG GAG ATC       629
Glu Tyr Ile Ser Asn Thr Phe Leu Asp Lys Gln Asn Asp Val Glu Ile
                105                 110                 115

CCA TCT CCT ACC CAG AAA GAC AGG GAG AAA AAG AAA AAG CAG CAG CTC       677
Pro Ser Pro Thr Gln Lys Asp Arg Glu Lys Lys Lys Lys Gln Gln Leu
                120                 125                 130

ATG ACC CAG ATA AGT GGA GTG AAG AAA TTA ATG CAT AGT TCA AGC CTA       725
Met Thr Gln Ile Ser Gly Val Lys Lys Leu Met His Ser Ser Ser Leu
                135                 140                 145

AAC AAT ACA AGC ATC TCA CGC TTT GGA GTC AAC ACT GAA AAT GAA GAT       773
Asn Asn Thr Ser Ile Ser Arg Phe Gly Val Asn Thr Glu Asn Glu Asp
            150                 155                 160

CAC CTG GCC AAG GAG CTG GAA GAC CTG AAC AAA TGG GGT CTT AAC ATC       821
His Leu Ala Lys Glu Leu Glu Asp Leu Asn Lys Trp Gly Leu Asn Ile
165                 170                 175                 180

TTT AAT GTG GCT GGA TAT TCT CAC AAT AGA CCC CTA ACA TGC ATC ATG       869
Phe Asn Val Ala Gly Tyr Ser His Asn Arg Pro Leu Thr Cys Ile Met
                185                 190                 195

TAT GCT ATA TTC CAG GAA AGA GAC CTC CTA AAG ACA TTC AGA ATC TCA       917
Tyr Ala Ile Phe Gln Glu Arg Asp Leu Leu Lys Thr Phe Arg Ile Ser
                200                 205                 210

TCT GAC ACA TTT ATA ACC TAC ATG ATG ACT TTA GAA GAC CAT TAC CAT       965
Ser Asp Thr Phe Ile Thr Tyr Met Met Thr Leu Glu Asp His Tyr His
                215                 220                 225

TCT GAC GTG GCA TAT CAC AAC AGC CTG CAC GCT GCT GAT GTA GCC CAG      1013
Ser Asp Val Ala Tyr His Asn Ser Leu His Ala Ala Asp Val Ala Gln
            230                 235                 240

TCG ACC CAT GTT CTC CTT TCT ACA CCA GCA TTA GAC GCT GTC TTC ACA      1061
Ser Thr His Val Leu Leu Ser Thr Pro Ala Leu Asp Ala Val Phe Thr
245                 250                 255                 260

GAT TTG GAG ATC CTG GCT GCC ATT TTT GCA GCT GCC ATC CAT GAC GTT      1109
Asp Leu Glu Ile Leu Ala Ala Ile Phe Ala Ala Ala Ile His Asp Val
                265                 270                 275
```

```
GAT CAT CCT GGA GTC TCC AAT CAG TTT CTC ATC AAC ACA AAT TCA GAA     1157
Asp His Pro Gly Val Ser Asn Gln Phe Leu Ile Asn Thr Asn Ser Glu
        280                 285                 290

CTT GCT TTG ATG TAT AAT GAT GAA TCT GTG TTG GAA AAT CAT CAC CTT     1205
Leu Ala Leu Met Tyr Asn Asp Glu Ser Val Leu Glu Asn His His Leu
            295                 300                 305

GCT GTG GGT TTC AAA CTG CTG CAA GAA GAA CAC TGT GAC ATC TTC ATG     1253
Ala Val Gly Phe Lys Leu Leu Gln Glu Glu His Cys Asp Ile Phe Met
310                 315                 320

AAT CTC ACC AAG AAG CAG CGT CAG ACA CTC AGG AAG ATG GTT ATT GAC     1301
Asn Leu Thr Lys Lys Gln Arg Gln Thr Leu Arg Lys Met Val Ile Asp
325                 330                 335                 340

ATG GTG TTA GCA ACT GAT ATG TCT AAA CAT ATG AGC CTG CTG GCA GAC     1349
Met Val Leu Ala Thr Asp Met Ser Lys His Met Ser Leu Leu Ala Asp
                345                 350                 355

CTG AAG ACA ATG GTA GAA ACG AAG AAA GTT ACA AGT TCA GGC GTT CTT     1397
Leu Lys Thr Met Val Glu Thr Lys Lys Val Thr Ser Ser Gly Val Leu
            360                 365                 370

CTC CTA GAC AAC TAT ACC GAT CGC ATT CAG GTC CTT CGC AAC ATG GTA     1445
Leu Leu Asp Asn Tyr Thr Asp Arg Ile Gln Val Leu Arg Asn Met Val
        375                 380                 385

CAC TGT GCA GAC CTG AGC AAC CCC ACC AAG TCC TTG GAA TTG TAT CGG     1493
His Cys Ala Asp Leu Ser Asn Pro Thr Lys Ser Leu Glu Leu Tyr Arg
        390                 395                 400

CAA TGG ACA GAC CGC ATC ATG GAG GAA TTT TTC CAG CAG GGA GAC AAA     1541
Gln Trp Thr Asp Arg Ile Met Glu Glu Phe Phe Gln Gln Gly Asp Lys
405                 410                 415                 420

GAG CGG GAG AGG GGA ATG GAA ATT AGC CCA ATG TGT GAT AAA CAC ACA     1589
Glu Arg Glu Arg Gly Met Glu Ile Ser Pro Met Cys Asp Lys His Thr
                425                 430                 435

GCT TCT GTG GAA AAA TCC CAG GTT GGT TTC ATC GAC TAC ATT GTC CAT     1637
Ala Ser Val Glu Lys Ser Gln Val Gly Phe Ile Asp Tyr Ile Val His
            440                 445                 450

CCA TTG TGG GAG ACA TGG GCA GAT TTG GTA CAG CCT GAT GCT CAG GAC     1685
Pro Leu Trp Glu Thr Trp Ala Asp Leu Val Gln Pro Asp Ala Gln Asp
        455                 460                 465

ATT CTC GAT ACC TTA GAA GAT AAC AGG AAC TGG TAT CAG AGC ATG ATA     1733
Ile Leu Asp Thr Leu Glu Asp Asn Arg Asn Trp Tyr Gln Ser Met Ile
        470                 475                 480

CCT CAA AGT CCC TCA CCA CCG CTG GAC GAG CAG AAC AGG GAC TGC CAG     1781
Pro Gln Ser Pro Ser Pro Pro Leu Asp Glu Gln Asn Arg Asp Cys Gln
485                 490                 495                 500

GGT CTG ATG GAG AAG TTT CAG TTT GAA CTG ACT CTC GAT GAG GAA GAT     1829
Gly Leu Met Glu Lys Phe Gln Phe Glu Leu Thr Leu Asp Glu Glu Asp
                505                 510                 515

TCT GAA GGA CCT GAG AAG GAG GGA GAG GGA CAC AGC TAT TTC AGC AGC     1877
Ser Glu Gly Pro Glu Lys Glu Gly Glu Gly His Ser Tyr Phe Ser Ser
            520                 525                 530

ACA AAG ACG CTT TGT GTG ATT GAT CCA GAA AAC AGA GAT TCC CTG GGA     1925
Thr Lys Thr Leu Cys Val Ile Asp Pro Glu Asn Arg Asp Ser Leu Gly
        535                 540                 545

GAG ACT GAC ATA GAC ATT GCA ACA GAA GAC AAG TCC CCC GTG GAT ACA     1973
Glu Thr Asp Ile Asp Ile Ala Thr Glu Asp Lys Ser Pro Val Asp Thr
        550                 555                 560

TAATCCCCCT CTCCCTGTGG AGATGAACAT TCTATCCTTG ATGAGCATGC CAGCTATGTG   2033

GTAGGGCCAG CCCACCATGG GGGCCAAGAC CTGCACAGGA CAAGGGCCAC CTGGCTTTCA   2093

GTTACTTGAG TTTGGAGTCA GAAAGCAAGA CCAGGAAGCA AATAGCAGCT CAGGAAATCC   2153

CACGGTTGAC TTGCCTTGAT GGCAAGCTTG GTGGAGAGGG CTGAAGCTGT TGCTGGGGGC   2213
```

-continued

```
CGATTCTGAT CAAGACACAT GGCTTGAAAA TGGAAGACAC AAAACTGAGA GATCATTCTG    2273

CACTAAGTTT CGGGAACTTA TCCCCGACAG TGACTGAACT CACTGACTAA TAACTTCATT    2333

TATGAATCTT CTCACTTGTC CCTTTGTCTG CCAACCTGTG TGCCTTTTTT GTAAAACATT    2393

TTCATGTCTT TAAAATGCCT GTTGAATACC TGGAGTTTAG TATCAACTTC TACACAGATA    2453

AGCTTTCAAA GTTGACAAAC TTTTTTGACT CTTTCTGGAA AAGGGAAAGA AAATAGTCTT    2513

CCTTCTTTCT TGGGCAATAT CCTTCACTTT ACTACAGTTA CTTTTGCAAA CAGACAGAAA    2573

GGATACACTT CTAACCACAT TTTACTTCCT TCCCCTGTTG TCCAGTCCAA CTCCACAGTC    2633

ACTCTTAAAA CTTCTCTCTG TTTGCCTGCC TCCAACAGTA CTTTTAACTT TTTGCTGTAA    2693

ACAGAATAAA ATTGAACAAA TTAGGGGGTA GAAAGGAGCA GTGGTGTCGT TCACCGTGAG    2753

AGTCTGCATA GAACTCAGCA GTGTGCCCTG CTGTGTCTTG GACCCTGCCC CCCACAGGAG    2813

TTGTACAGTC CCTGGCCCTG CTCCCTACCT CCTCTCTTCA CCCCGTTAGG CTGTTTTCAA    2873

TGTAATGCTG CCGTCCTTCT CTTGCACTGC CTTCTGCGCT AACACCTCCA TTCCTGTTTA    2933

TAACCGTGTA TTTATTACTT AATGTATATA ATGTAATGTT TTGTAAGTTA TTAATTTATA    2993

TATCTAACAT TGCCTGCCAA TGGTGGTGTT AAATTTGTGT AGAAAACTCT GCCTAAGAGT    3053

TACGACTTTT TCTTGTAATG TTTTGTATTG TGTATTATAT AACCCAAACG TCACTTAGTA    3113

GAGACATATG GCCCCCTTGG CAGAGAGGAC AGGGGTGGGC TTTTGTTCAA AGGGTCTGCC    3173

CTTTCCCTGC CTGAGTTGCT ACTTCTGCAC AACCCCTTTA TGAACCAGTT TTGGAAACAA    3233

TATTCTACAC ATTAGATACT AAATGGTTTA TACTGAGCTT TTACTTTTGT ATAGCTTGAT    3293

AGGGGCAGGG GGCAATGGAT GTAGTTTTTA CCCAGGTTCT ATCCAAATCT ATGTGGGCAT    3353

GAGTTGGGTT ATAACTGGAT CCTACTATCA TTGTGGCTTT GGTTCAAAAG GAAACACTAC    3413

ATTTGCTCAC AGATGATTCT TCTGAATGCT CCCGAACTAC TGACTTTGAA GAGGTAGCCT    3473

CCTGCCTGCC ATTAAGCAGG AATGTCATGT TCCAGTTCAT TACAAAAGAA AACAATAAAA    3533

CAATGTGAAT TTTTATAATA AAATGTGAAC TGATGTAGCA AATTACGCAA ATGTGAAGCC    3593

TCTTCTGATA ACACTTGTTA GGCCTCTTAC TGATGTCAGT TTCAGTTTGT AAAATATGTT    3653

TCATGCTTTC AGTTCAGCAT TGTGACTCAG TAAATACAGA AAATGGCACA AATGTGCATG    3713

ACCAATGTAT GTCTATGAAC ACTGCATTGT TTCAGGTGGA CATTTTATCG ATTTTCAAAT    3773

GTTTCTCACA ATGTATGTTA TAGTGTTATT ATTATATATT GTGTTCAAAT GCATTCTAAA    3833

GAGACTTTTA TATGAGGTGA ATAAAGAAAA GCATAATTAA AAAAAAAAAA AAAAAAA      3890
```

(2) INFORMATION FOR SEQ ID NO:2:

(i) SEQUENCE CHARACTERISTICS:
        (A) LENGTH: 564 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Glu His Gly Gly Thr Phe Ser Ser Thr Gly Ile Ser Gly Gly
 1               5                  10                  15

Ser Gly Asp Ser Ala Met Asp Ser Leu Gln Pro Leu Gln Pro Asn Tyr
            20                  25                  30

Met Pro Val Cys Leu Phe Ala Glu Glu Ser Tyr Gln Lys Leu Ala Met
        35                  40                  45

Glu Thr Leu Glu Glu Leu Asp Trp Cys Leu Asp Gln Leu Glu Thr Ile
```

```
                50                  55                  60
Gln Thr Tyr Arg Ser Val Ser Glu Met Ala Ser Asn Lys Phe Lys Arg
 65                  70                  75                  80
Met Leu Asn Arg Glu Leu Thr His Leu Ser Glu Met Ser Arg Ser Gly
                    85                  90                  95
Asn Gln Val Ser Glu Tyr Ile Ser Asn Thr Phe Leu Asp Lys Gln Asn
                100                 105                 110
Asp Val Glu Ile Pro Ser Pro Thr Gln Lys Asp Arg Glu Lys Lys Lys
                115                 120                 125
Lys Gln Gln Leu Met Thr Gln Ile Ser Gly Val Lys Lys Leu Met His
                130                 135                 140
Ser Ser Ser Leu Asn Asn Thr Ser Ile Ser Arg Phe Gly Val Asn Thr
145                 150                 155                 160
Glu Asn Glu Asp His Leu Ala Lys Glu Leu Glu Asp Leu Asn Lys Trp
                165                 170                 175
Gly Leu Asn Ile Phe Asn Val Ala Gly Tyr Ser His Asn Arg Pro Leu
                180                 185                 190
Thr Cys Ile Met Tyr Ala Ile Phe Gln Glu Arg Asp Leu Leu Lys Thr
                195                 200                 205
Phe Arg Ile Ser Ser Asp Thr Phe Ile Thr Tyr Met Met Thr Leu Glu
210                 215                 220
Asp His Tyr His Ser Asp Val Ala Tyr His Asn Ser Leu His Ala Ala
225                 230                 235                 240
Asp Val Ala Gln Ser Thr His Val Leu Leu Ser Thr Pro Ala Leu Asp
                245                 250                 255
Ala Val Phe Thr Asp Leu Glu Ile Leu Ala Ala Ile Phe Ala Ala Ala
                260                 265                 270
Ile His Asp Val Asp His Pro Gly Val Ser Asn Gln Phe Leu Ile Asn
                275                 280                 285
Thr Asn Ser Glu Leu Ala Leu Met Tyr Asn Asp Glu Ser Val Leu Glu
                290                 295                 300
Asn His His Leu Ala Val Gly Phe Lys Leu Leu Gln Glu Glu His Cys
305                 310                 315                 320
Asp Ile Phe Met Asn Leu Thr Lys Lys Gln Arg Gln Thr Leu Arg Lys
                325                 330                 335
Met Val Ile Asp Met Val Leu Ala Thr Asp Met Ser Lys His Met Ser
                340                 345                 350
Leu Leu Ala Asp Leu Lys Thr Met Val Glu Thr Lys Lys Val Thr Ser
                355                 360                 365
Ser Gly Val Leu Leu Leu Asp Asn Tyr Thr Asp Arg Ile Gln Val Leu
                370                 375                 380
Arg Asn Met Val His Cys Ala Asp Leu Ser Asn Pro Thr Lys Ser Leu
385                 390                 395                 400
Glu Leu Tyr Arg Gln Trp Thr Asp Arg Ile Met Glu Glu Phe Phe Gln
                405                 410                 415
Gln Gly Asp Lys Glu Arg Glu Arg Gly Met Glu Ile Ser Pro Met Cys
                420                 425                 430
Asp Lys His Thr Ala Ser Val Glu Lys Ser Gln Val Gly Phe Ile Asp
                435                 440                 445
Tyr Ile Val His Pro Leu Trp Glu Thr Trp Ala Asp Leu Val Gln Pro
                450                 455                 460
Asp Ala Gln Asp Ile Leu Asp Thr Leu Glu Asp Asn Arg Asn Trp Tyr
465                 470                 475                 480
```

```
Gln Ser Met Ile Pro Gln Ser Pro Ser Pro Leu Asp Glu Gln Asn
                485                 490                 495

Arg Asp Cys Gln Gly Leu Met Glu Lys Phe Gln Phe Glu Leu Thr Leu
            500                 505                 510

Asp Glu Glu Asp Ser Glu Gly Pro Lys Glu Gly Glu Gly His Ser
        515                 520                 525

Tyr Phe Ser Ser Thr Lys Thr Leu Cys Val Ile Asp Pro Glu Asn Arg
        530                 535                 540

Asp Ser Leu Gly Glu Thr Asp Ile Asp Ile Ala Thr Glu Asp Lys Ser
545                 550                 555                 560

Pro Val Asp Thr
```

(2) INFORMATION FOR SEQ ID NO:3:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens
        (F) TISSUE TYPE: brain (ix) FEATURE:
        (A) NAME/KEY: misc_feature
        (B) LOCATION: 1..40
        (D) OTHER INFORMATION: /function= "5' PCR probe"

(xi) SEQUENCE DESCRIPTION: SEQ ID NO:3:

GGGGCTCGAG GAGGGACACA CGTATTTCAG CAGCACAAAG                    40

(2) INFORMATION FOR SEQ ID NO:4:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (B) STRAIN: Homo sapiens
        (F) TISSUE TYPE: brain (ix) FEATURE:
        (A) NAME/KEY: misc_feature
        (B) LOCATION: 1..40
        (D) OTHER INFORMATION: /function= "3' PCR probe"

(xi) SEQUENCE DESCRIPTION: SEQ ID NO:4:

CTCACTTGAG TGACTGATTA TTGAAGTAAA GAGCTCGGGG                    40

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo Sapiens

```
            (F) TISSUE TYPE: brain (ix) FEATURE:
            (A) NAME/KEY: misc_feature
            (B) LOCATION: 1..42
            (D) OTHER INFORMATION: /function= "5' PCR probe"

(xi) SEQUENCE DESCRIPTION: SEQ ID NO:5:

GGGGGCTCGA GAATGAAGGA GCACGGGGGC ACCTTCAGTA GC                           42

(2) INFORMATION FOR SEQ ID NO:6:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (vi) ORIGINAL SOURCE:
            (A) ORGANISM: Homo sapiens
            (F) TISSUE TYPE: Brain (ix) FEATURE:
            (A) NAME/KEY: misc_feature
            (B) LOCATION: 1..30
            (D) OTHER INFORMATION: /function= "3' PCR probe"

(xi) SEQUENCE DESCRIPTION: SEQ ID NO:6:

GACGGTAAAA ACGTCGACGG TAGGTACTGC                                        30
```